US008663606B2

(12) United States Patent
Mundus et al.

(10) Patent No.: US 8,663,606 B2
(45) Date of Patent: *Mar. 4, 2014

(54) METHOD OF PRODUCING A CATIONIC LIPOSOMAL PREPARATION COMPRISING A LIPOPHILIC COMPOUND

(75) Inventors: Carsten Mundus, Ummendorf/Fischbach (DE); Christian Welz, Brixlegg (AT); Oliver Schramel, Ismaning (DE); Heinrich Haas, Munich (DE); Thomas Fichert, Oberthal (DE); Brita Schulze, Walchensee (DE); Toralf Peymann, Munich (DE); Uwe Michaelis, Weilheim (DE); Michael Teifel, Weiterstadt (DE); Friedrich Gruber, Krailling (DE); Gerhard Winter, Penzberg (DE)

(73) Assignee: Medigene AG, Planegg/Martinsried (DE)

( * ) Notice: Subject to any disclaimer, the term of this patent is extended or adjusted under 35 U.S.C. 154(b) by 74 days.

This patent is subject to a terminal disclaimer.

(21) Appl. No.: 13/278,801

(22) Filed: Oct. 21, 2011

(65) Prior Publication Data

US 2012/0087975 A1   Apr. 12, 2012

Related U.S. Application Data

(60) Continuation of application No. 12/859,000, filed on Aug. 18, 2010, now Pat. No. 8,075,913, which is a division of application No. 11/018,574, filed on Dec. 22, 2004, now Pat. No. 7,794,747, which is a continuation-in-part of application No. PCT/EP03/06759, filed on Jun. 26, 2003.

(60) Provisional application No. 60/391,245, filed on Jun. 26, 2002, provisional application No. 60/391,246, filed on Jun. 26, 2002.

(30) Foreign Application Priority Data

Aug. 21, 2002 (EP) .................................... 02018724
Mar. 4, 2003 (EP) .................................... 03004744

(51) Int. Cl.
*A61K 9/127* (2006.01)
*A61K 31/685* (2006.01)
*A61K 31/56* (2006.01)
*A61K 31/4375* (2006.01)
*A61K 31/427* (2006.01)
*A61K 31/337* (2006.01)

(52) U.S. Cl.
USPC .............. 424/45; 514/76; 514/182; 514/283; 514/365; 514/449

(58) Field of Classification Search
None
See application file for complete search history.

(56) References Cited

U.S. PATENT DOCUMENTS

| | | | |
|---|---|---|---|
| 5,415,869 A | 5/1995 | Straubinger et al. | |
| 5,424,073 A | 6/1995 | Rahman | |
| 5,549,910 A | 8/1996 | Szoka | |
| 5,578,320 A | 11/1996 | Janoff et al. | |
| 5,648,090 A | 7/1997 | Rahman | |
| 5,653,998 A | 8/1997 | Hamann | |
| 5,683,715 A | 11/1997 | Boni | |
| 5,733,888 A | 3/1998 | Carver | |
| 5,821,263 A | 10/1998 | Scola et al. | |
| 5,869,680 A | 2/1999 | Mas et al. | |
| 6,034,072 A | 3/2000 | Bruno et al. | |
| 6,090,955 A | 7/2000 | Reszka et al. | |
| 6,120,798 A | 9/2000 | Allen et al. | |
| 6,140,359 A | 10/2000 | Carver et al. | |
| 6,306,894 B1 | 10/2001 | Carver et al. | |
| 7,112,338 B2 | 9/2006 | McDonald et al. | |
| 7,794,747 B2 * | 9/2010 | Mundus et al. | 424/450 |
| 2002/0034537 A1 | 3/2002 | Michaelis et al. | |
| 2002/0090392 A1 * | 7/2002 | Campbell et al. | 424/450 |
| 2003/0187062 A1 | 10/2003 | Zenoni et al. | |
| 2011/0159052 A1 | 6/2011 | Deluca et al. | |

FOREIGN PATENT DOCUMENTS

| | | |
|---|---|---|
| EP | 1 059 092 | 7/2005 |
| JP | 6-211645 | 1/1993 |
| JP | 2002-508765 | 3/2002 |
| WO | 95/03795 A1 | 2/1995 |
| WO | 98/22451 | 5/1998 |
| WO | 98/28288 | 7/1998 |
| WO | 98/40052 | 9/1998 |
| WO | 98/51278 | 11/1998 |
| WO | 98/58630 | 12/1998 |
| WO | 99/09021 | 2/1999 |
| WO | 99/14209 | 3/1999 |
| WO | 99/18113 | 4/1999 |
| WO | 99/65465 | 12/1999 |
| WO | 00/61543 | 10/2000 |
| WO | 01/05374 | 1/2001 |

(Continued)

OTHER PUBLICATIONS

Campbell et al. (J Pharm Sci. Aug. 8, 2001; 90(8):1091-1105).*
Straubinger et al. (Methods in Enzymology: Taxane-Containing Liposomes. 2005; 391: 97-117).*
Balasubramanian and Straubinger, Taxol-Lipid Interactions: Taxol-Dependent effects on the physical properties of model membranes, Biochemistry 1994, 33, 8941-8947.
Nichols et al., "Net proton-hydroxyl permeability of large unilamellar liposomes measured by an acid-base titration technique", Proc. Natl. Acad. Sci., Apr. 1980, vol. 77, pp. 2038-2042.
Szoka et al., "Comparative properties and methods of preparation of lipid vesicles (liposomes)", Ann. Rev. Biophys. Bioeng., 1980, vol. 9, pp. 467-508.

(Continued)

*Primary Examiner* — Scott Long
(74) *Attorney, Agent, or Firm* — Dentons US LLP

(57) ABSTRACT

A method for producing a cationic liposomal preparation comprising a lipophilic active compound with physical and chemical stability during manufacturing, storing and reconstituting, and further a cationic liposomal preparation obtainable by this method as well as specific cationic liposomal preparations as well as pharmaceutical compositions are disclosed.

22 Claims, 9 Drawing Sheets

(56) References Cited

FOREIGN PATENT DOCUMENTS

| WO | 01/10412 | 2/2001 |
|---|---|---|
| WO | 01/17508 | 3/2001 |
| WO | 01/25223 | 4/2001 |
| WO | 01/56548 | 8/2001 |
| WO | 01/82899 | 11/2001 |
| WO | 01/93836 | 12/2001 |

OTHER PUBLICATIONS

Dua et al., "Liposome: methods of preparation and applications", International Journal of Pharmaceutical Studies and Research, 2012, vol. 3, pp. 14-20.

Michaelis et al., "Targeting of Cationic Liposomes to Endothelial Tissue", Liposome Technology, Third edition, 2007, vol. 3, chapter 9, pp. 151-170, Informa Healthcare.

Regueiro-Ren, et al., SAR and pH Stability of Cyano-Substituted Epothilones, Org. Lett., 2002, 4:3815-3818.

Lee, et al., BMS-247550: A novel epothilone analog with a mode of action similar to paclitaxel but possessing superior antitumor efficacy, Clin. Cancer Res., 2001, 7:1429-1437.

Grit, et al., Chemical stability of liposomes: implications for their physical stability, Chemistry and Physics of Lipids, 1993, 64:3-18.

Nicolaou, et al., Recent developments in the chemistry, biology and medicine of the epothilones, Chem. Comm., 2001, 1523-1535.

Altmann, et al., Epothilones and related structures, Biochim. Et Biophys. Acta, 2000, 1470:M79-M91.

Seftow, et al., Derivatization of the C12-C13 functional groups of epothilones A, B and C, Bioorg. & Medicinal Chem. Lett., 1998, 8:3031-3036.

Zuidam, et al., Chemical Hydrolysis of Phospholipids, Journal of Pharmaceutical Sciences, 1995, 84:1113-1119.

Stachel, et al., On the total synthesis and preliminary biological evaluations of 15(R) and 15(S) Aza-dEpoB, Org. Lett., 2000, 2:1637-1639.

Sharma, et al., Novel Taxol Formulations: Preparation and Characterization of Taxol-Containing Liposomes, Pharmaceutical Research, 1994, 11(6):889-896.

Sharma, et al., Antitumor effect of taxol-containing liposomes in a taxol-resistant murine tumor model, Cancer Res, 1993, 53:5877-81.

Sharma, et al., Activity of Paclitaxel Liposome Formulations Against Human Ovarian Tumor Xenografts, Int. J. Cancer, 1997, 71:103-107.

Chou, et al., The synthesis, discovery and development of a highly promising class of microtubule stabilization agents, PNAS, 2001, 98:8113-8118.

Thurston, et al., Cationic liposomes target angiogenic endothelial cells in tumors and chronic inflammation in mice, J . Clin. Invest, 1998, 101(7):1401-13.

Vemooij, et al., Chemical hydrolysis of DOTAP and DOPE in a liposomal environment, Journal of Controlled Release, 2002, 79(1-3):299-303.

Crosasso, et al., Preparation, characterization and properties of sterically stabilized paclitaxel-containing liposomes, Journal of Controlled Release, 2000, 63:19-30.

Dordunoo, et al., Solubility and Stability of Taxol: effects of buffers and cyclodextrins, International Journal of Pharmaceutics, 1996, 133: 191-201.

Banerjee, J Biomater Appl. 2001, 16(1): 3-21.

Campbell, et al., Influence of cationic lipids on the stability and membrane properties of paclitaxel-containing liposomes, J Pharm Sci, 2001, 90(8): 1091-1105.

Ceruti, et al., Preparation, characterization, cytotoxicity and pharmacokinetics of liposomes containing water-soluble prodrugs of paclitaxel, Journal of Controlled Release, 2000, 63(1-2): 141-153.

Straubinger, et al., Preparation and Characterization of Taxane-Containing Liposomes, Methods in Enzymology, 2005, 391:97-117.

Encyclopedia of Surface and Colloid Science, vol. 1: A-Dif, edited by A. T. Hubbard (2002).

Documents in EP 03740355.7 Opposition.

\* cited by examiner

Fig 1: Liposomal diameter and PI values for LipoPac™ (Batch GB 100)
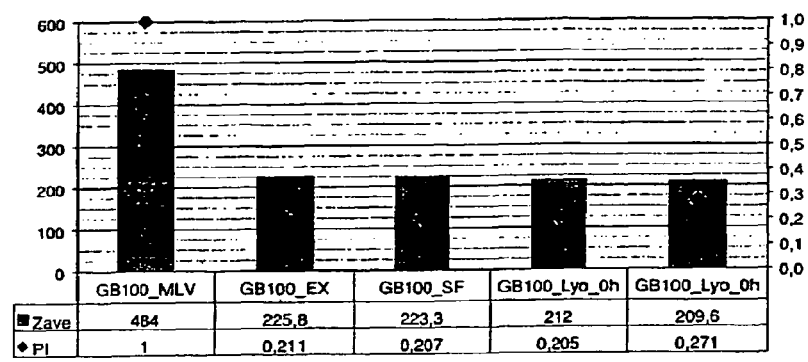
Fig 2: Liposomal diameter and PI values for LipoPac™ (Batch GB 261)
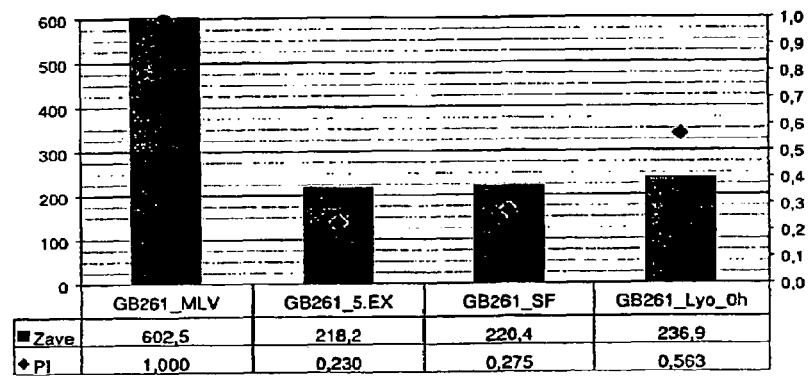

Fig 4: Particle counts (0-8h)
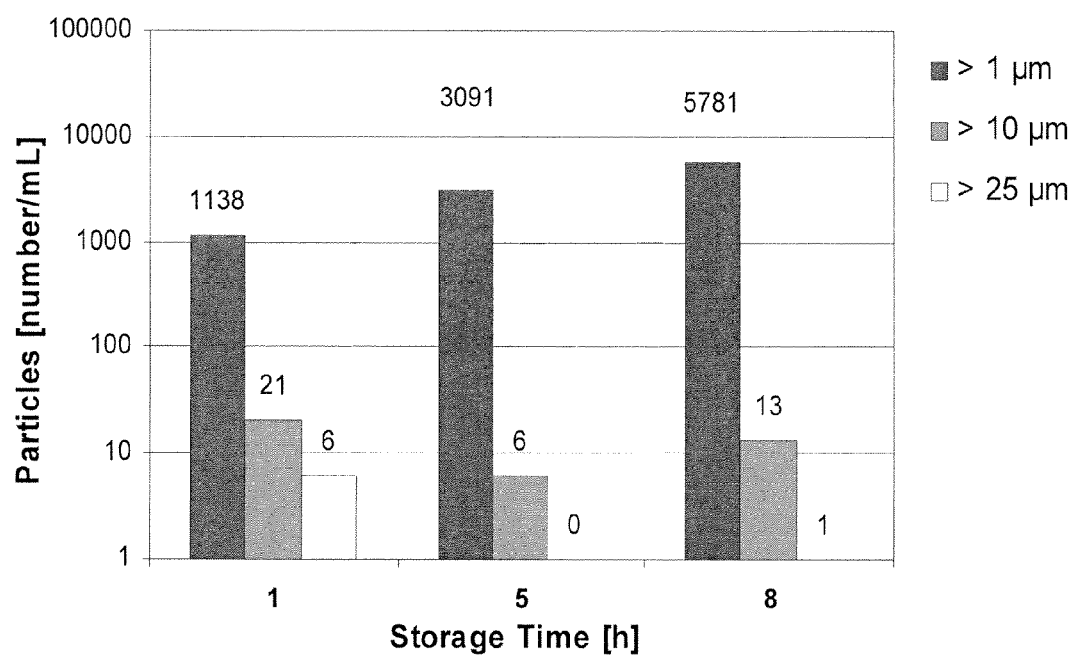

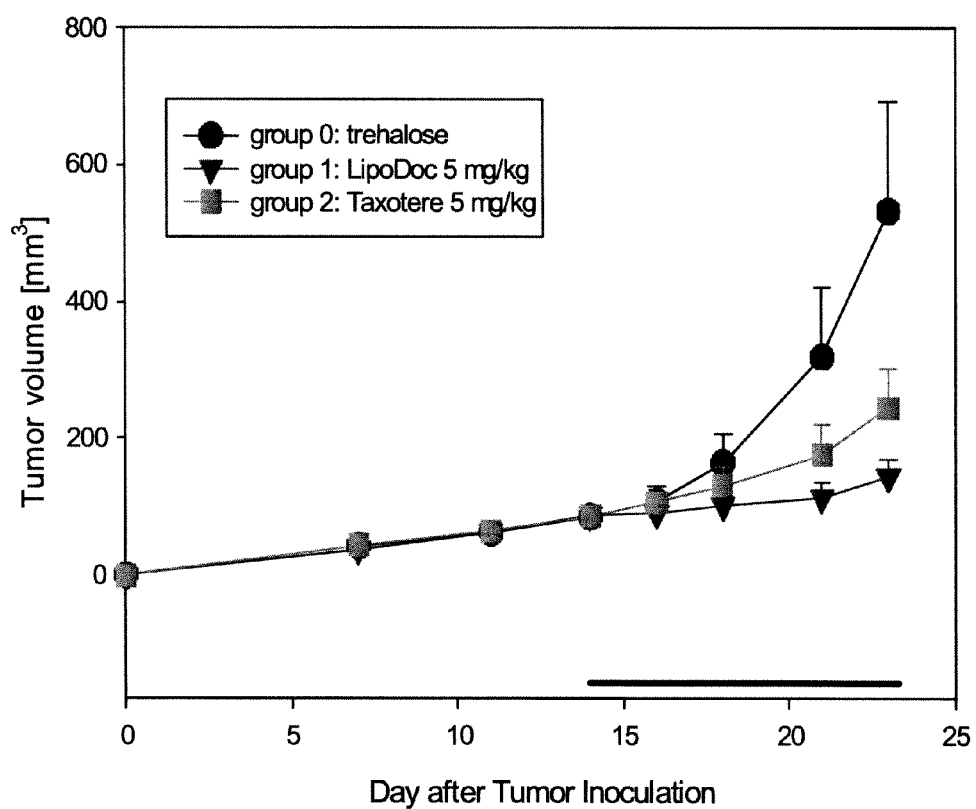
Fig 5: Therapeutic efficacy of LipoDoc™ vs. Taxotere® in A-375 melanoma in nude mice

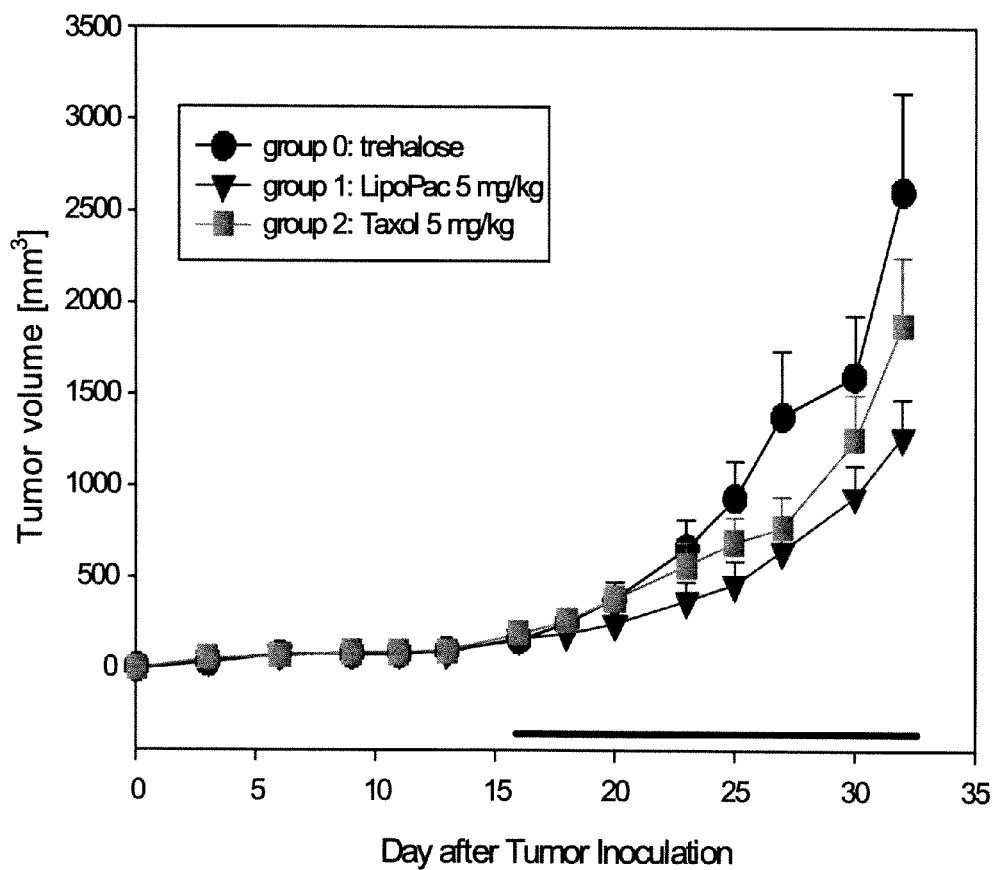
Fig 6: Therapeutic efficacy of LipoPac™ vs. Taxol® in A-375 melanoma in nude mice

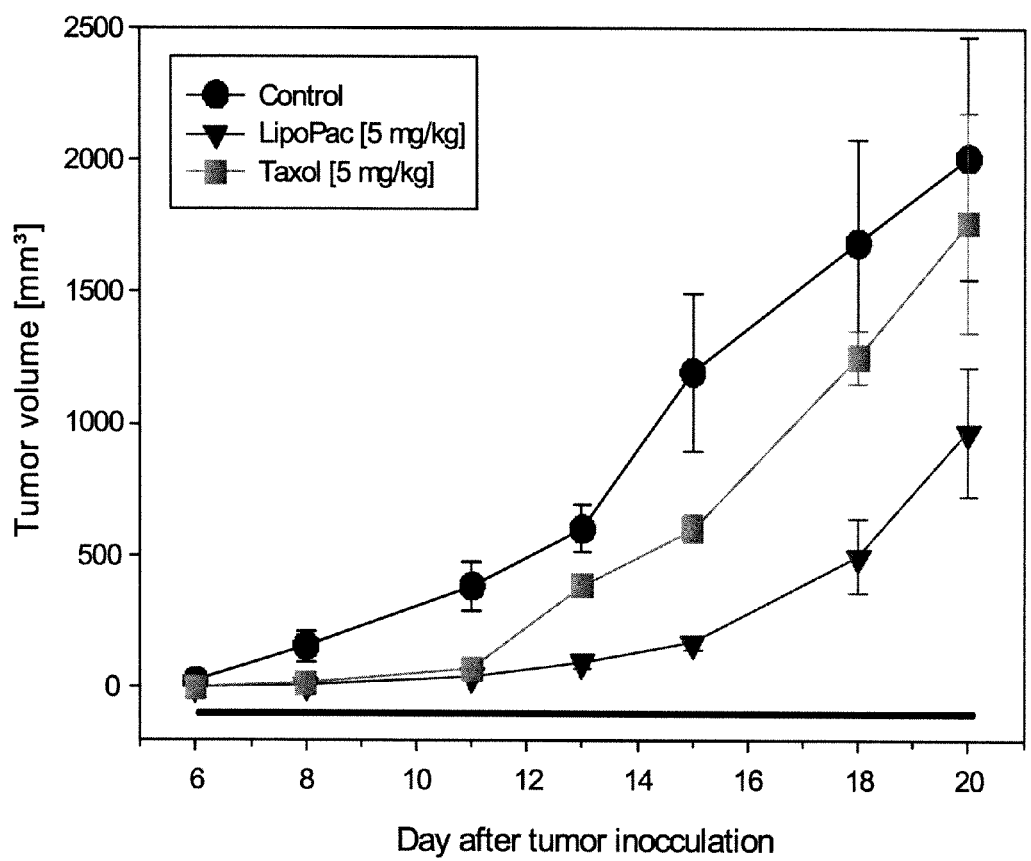
Fig 7: Therapeutic efficacy of LipoPac™ vs. Taxol® in B-16 melanoma in C57/BL6 mice

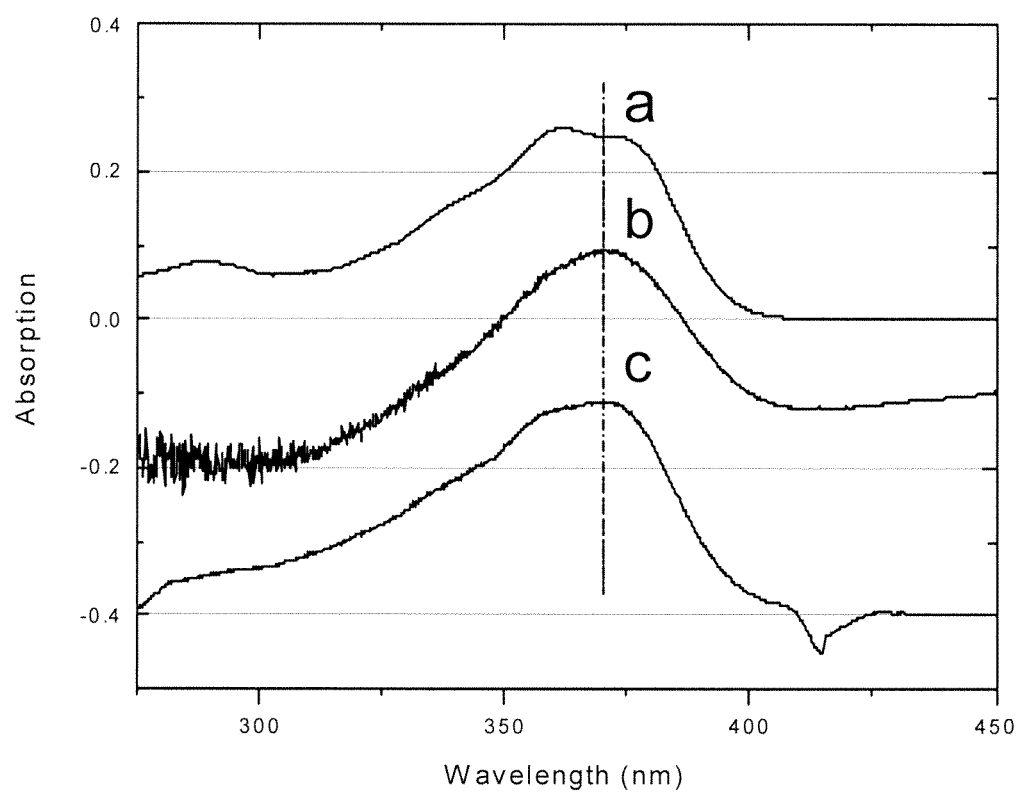
Fig 8: UV-VIS Spectra of Camptothecin

METHOD OF PRODUCING A CATIONIC LIPOSOMAL PREPARATION COMPRISING A LIPOPHILIC COMPOUND

The present application is a continuation of U.S. Ser. No. 12/859,000, filed on Aug. 18, 2010, now U.S. Pat. No. 8,075,913 which is a divisional of U.S. application Ser. No. 11/018,574, filed Dec. 22, 2004, U.S. Pat. No. 7,794,747, which is a Continuation-in-Part of PCT/EP2003/006759, filed on Jun. 26, 2003, which claims the benefit of priority of U.S. Provisional Application 60/391,245, filed Jun. 26, 2002; U.S. Provisional Application 60/391,246, filed Jun. 26, 2002; European Application EP 02018724.1, filed Aug. 21, 2002; and European Application EP 03004744.3, filed Mar. 4, 2003, all of which are herein incorporated by reference in their entirety.

The present invention relates to a method for producing a cationic liposomal preparation containing a lipophilic active compound, e.g. a taxane, having high stability which is suitable for therapeutic applications.

Liposomes are small, spherical vesicles composed primarily of various types of lipids, phospholipids and other lipophilic components. The lipid components normally form a bilayer, where the polar end of the amphiphile is in contact with the surrounding solution, which is typically an aqueous solution. The non-polar, hydrophobic end of the amphiphile is in contact with another non-polar, hydrophobic end of another amphiphile thereby forming the lipid bilayer. Depending on the type of amphiphiles used, the liposome membrane can be classified according to their outer charge into net neutral, negatively and positively charged membranes.

Liposomes have been developed for many therapeutic and diagnostic applications. Among others they are used to deliver molecules which are not sufficiently soluble in water. These lipophilic molecules are incorporated into the liposome bilayer or have been chemically linked to the lipid bilayer.

Paclitaxel, the most prominent representative of the taxane family, is such a highly lipophilic compound. Paclitaxel is known as Taxol® which is the drug formulated in polyethoxylated castor oil (Cremophor® EL) and absolute ethanol. Additionally, paclitaxel has been formulated in liposomes.

Before Taxol® is applied to humans, the pharmaceutical carrier with the therapeutic compound is diluted in a suitable aqueous solution. The carrier, however, has been observed to cause serious, life-threatening anaphylactic reactions in animals and humans, and is physically incompatible with some intravenous infusion systems. Therefore, several attempts have been made to eliminate the Cremophor® EL by reformulating the drug in a better tolerated vehicle. Liposomes have been clinically characterized during the last decades and are known as a save and well tolerated drug delivery system. Liposomes may consist of naturally occurring lipids bearing a polar head group which is neutrally or negatively charged. Positively charged diacylglyceride lipids do not occur in nature.

Sharma et al. [1] manufactured neutral paclitaxel-liposomes according to the so-called film method. The lipids, phosphatidylcholine (PC) and phosphatidylglycerol (PG) were dissolved together with paclitaxel in chloroform. The chloroform was evaporated at 40° C. and the paclitaxel-lipid film dissolved in tert-butanol. The solution was aliquoted and lyophilized. The powder was hydrated with buffer (NaCl/Tes/EDTA: 140 mM/10 mM/0.1 mM) giving a crude liposome suspension, which was further processed in a bath sonicator at 20° C. Chemical stability of the drug has been shown in these formulations for more than 2 months at 4° C. and room temperature. The pH is specified in the physiological range of pH 7-7.5.

In U.S. Pat. No. 6,090,955 Rerska et al. described manufacturing of neutral paclitaxel liposomes from egg phosphatidylcholine according to the film method. The crude liposome suspension, pH 7.2-7.4, consisting of multi-layered vesicles (MLV) was homogenized with a high-pressure homogenizer. For longer storage gel formation or lyophilisation is suggested. However, no data were presented on stability, e.g. chemical stability of paclitaxel was not addressed.

Recently, it has been reported that cationic liposomes represent not only another variety of a liposomal carrier system but also show a specific targeting effect to neoangiogenic areas in blood vessels [2]. Cationic liposomes have been used frequently for gene delivery, but little is known about their formulation characteristics for other compounds as compared to neutral or anionic liposomes.

Campbell et al. [3] formulated paclitaxel liposomes with varying content of cationic lipid finding increased physical stability of the paclitaxel-containing liposomes. The liposomes were manufactured according to the film-method. The film was hydrated with water, which was heated to a temperature of 5-10° C. above the phase transition temperature of the respective phospholipid which was used. The liposomal suspension was then sonicated in a bath-type sonicator. The resulting liposomal diameter was in the range of 500-800 nm. It was noted that the physical stability of these liposomes was for a maximum of 3 days. The conditions like temperature and pH in which these liposomes were kept were not disclosed. For a pharmaceutical formulation a stability of a few days is, however, not sufficient if applied for clinical purposes.

Another class of highly lipophilic molecules are the epothilones, specifically epothilone A and B. For both compounds, lack of stability at low pH has been described and is attributed to acid catalyzed ring opening reactions of the epoxide moiety. This lead to reaction products which had lost their exceptional cytotoxic properties. [9] The apparent instability of epothilone A and B does not allow the development of oral formulations of epothilone A or B, since stomach pH is around 1-3 and would rapidly degrade the cytostatic epothilone A or B [10].

The plasma half life especially of epothilone B has been reported to be extremely low due to its metabolic degradation via esterases. [11, 12] This holds true also for other epothilones; in murine plasma, the approximate in vitro half life of desoxy-epothilone B (epothilone D) was found to be 20 min, in human plasma the half life was around 3 h [13]. This does not allow a continuous high level drug exposure of the tumor and unsatisfactory in vivo antitumor activity of epothilones A and B have been attributed to their poor metabolic stability [12].

Liposomal compositions of epothilones A or B have been described. [WO 01/10412 A1]. Here, the general instability of these epothilones is referred to and this is given as a rationale for liposomal loading. However, no data is presented to support that the stability of liposomal epothilones is enhanced over that of nonliposomal epothilones.

Most of the preparation steps for the manufacturing of liposomes are performed in an aqueous environment (formation of the vesicles, homogenisation and/or removal of undesired components, reconstitution of lyophilized formulations). During these steps the liposomal components as well as active ingredients which are loaded into the liposomal membrane are prone to degradation.

The physicochemical stability of liposomes containing drugs is a limiting factor for the development of a pharmaceutical product with a shelf life sufficient for storage, distribution and application to humans after manufacturing.

One approach to increase the physicochemical stability of drug-loaded liposomes is to remove water quantitatively from the liposomal suspension. Methods that have been successfully applied to remove water from liposomes are freeze-drying, spray-drying or evaporation. Typically, a liposomal suspension is manufactured by dispersing the amphiphile compounds in an aqueous environment. Immediately after manufacturing of the aqueous bulk material, the suspension is dehydrated by any suitable method and stored until application in dried state. During the drying process a stabilizing agent may be used to maintain the liposome structure. Water that is usually associated with the polar liposomal surface is replaced by the stabilizing agent during drying to maintain the liposomal physicochemical characteristics. The drug stays loaded or strongly associated in/with the liposomal membrane. Release of compounds is well controlled. In an optimal case, liposomal size and size distribution is not affected by the process and loaded compounds and lipids stay chemically intact. However, dehydrating of a cationic liposomal preparation comprising a lipophilic active compound was not disclosed yet.

Thus, the underlying problem of the present invention was to provide an improved method for producing a cationic liposomal preparation comprising a lipophilic active compound with improved physicochemical stability and pharmaceutical applicability.

The solution was to provide a method for producing a cationic liposomal preparation comprising at least one amphiphile selected from cationic lipids in an amount of at least about 30 mol %, optionally at least one further amphiphile in an amount of up to about 69.9 mol %, a lipophilic active compound in an amount of at least about 0.1 mol % and a stabilizing agent in an amount of about 0.1% (m/v) to about 20% (m/v), comprising the steps of
a) providing
  i. an organic solution comprising an organic solvent, said active compound and said cationic lipid, and optionally said further amphiphile,
  ii. an aqueous solution comprising said stabilizing agent,
b) preparing a cationic liposomal preparation from said solution a) i. and a) ii., wherein said preparation comprises cationic liposomes in an aqueous medium,
c) optionally homogenising said preparation at least once and/or
d) optionally sterile filtrating said preparation,
e) dehydrating said preparation and
f) optionally reconstituting said cationic liposomes of step e) in an aqueous solution and
wherein optionally before step c) and/or d) an ultrafiltration step is included.

Preferred organic solvents to be used in step a) i. are, although not limited to these examples, selected from the following group: methanol, ethanol, propanol, isopropanol, ethylene glycol, tetrahydrofuran, chloroform, tert.-butanol or diethylether or a mixture of these solvents.

Any pharmacologically active lipophilic compound may be loaded into cationic liposomes of the present invention. Preferably, the active compound is selected from a therapeutically or diagnostically suitable lipophilic compound such as a cytostatic or cytotoxic agent or an imaging agent such as a dye, fluorescent dye and the like. Preferred therapeutically active compounds are selected from a taxane, from a camptothecin in its lactone form, from other agents interacting with microtubuli such as epothilones, discodermolide, laulimalide, isolaulimalide, eleutherobin, Sarcodictyin A and B, from a statin (e.g., lovastatin), from a depsipeptide, from other drugs such as thalidomide. Preferred diagnostically active compounds are selected from (i) poly-iodinated triglycerides (e.g., 2-oleoylglycerol-1,3-bis[7-(3-amino-2,4,6-triiodophenyl)heptanoate) or poly-iodinated oils such as Lipiodol, (ii) $^{99m}$Tc-HMPAO (hexamethyl propyleneamine dioxim) and derivatives thereof, (iii) fluorescent compounds such as rhodamine, (iv) lipid coated ferrite particles, (v) lipid coupled contrast agents for MRI (e.g., Gd chelators such as DOTA or DTPA coupled to a lipid or to a fatty acid), (vi) lipid coupled contrast agents for Xray (e.g. lipid coupled Iopamidol), (vii) lipid coupled chelators such as HYNIC or DTPA for scintigraphically useful nuclides such as $^{111}$In or $^{99m}$Tc, or (viii) lipid coupled fluorescent dyes such as rhodamine or Texas Red.

In a preferred embodiment the liposomal preparation comprises a taxane, preferably paclitaxel or docetaxel or a lipophilic derivative thereof in an amount of about 1 to about 20 mol %, preferably in an amount of about 2 to about 5 mol % paclitaxel, and preferably in an amount of at least 11 mol % for docetaxel or succinyl-paclitaxel. In a further preferred embodiment said liposomal preparation comprises camptothecin lactone in an amount of about 0.1 mol % to about 1 mol %.

Useful cationic lipids with respect to the present invention include but are not limited to:
DDAB, dimethyldioctadecyl ammonium bromide; N-[1'-(2,3-dioloyloxy)propyl]-N,N,N-trimethyl ammonium methylsulfate; 1,2-diacyloxy-3-trimethylammonium propanes, (including but not limited to, dioleoyl (DOTAP), dilauroyloxy, dimyristoyloxy, dipalmitoyloxy, and distearoyloxy); N-[1-(2,3-dioleoyloxy)propyl]-N,N-dimethyl amine; 1,2-diacyl-3-dimethylammonium propanes, (including but not limited to, dioleoyl (DODAP), dilauroyl. dimyristoyl, dipalmitoyl, and distearoyl); DOTMA, N-[1-[2,3-bis(oleyloxy)]propyl]-N,N,N-trimethylammonium chloride, (including but not limited to, dioleyl (DOTMA), dilauryl, dimyristyl, dipalmityl, and distearyl); DOGS, dioctadecylamidoglycylspermine; DC-cholesterol, 3β-[N—(N',N'-dimethylaminoethane)carbamoyl]cholesterol; DOSPA, 2,3-dioleoyloxy-N-(2-(sperminecarboxamido)-ethyl)-N,N-dimethyl-1-propanaminium trifluoroacetate; 1,2-diacyl-sn-glycero-3-ethylphosphocholines (including but not limited to dioleoyl (DOEPC), dilauroyl, dimyristoyl, dipalmitoyl, distearoyl, and palmitoyl-oleoyl); β-alanyl cholesterol; CTAB, cetyl trimethyl ammonium bromide; diC14-amidine, N-t-butyl-N'-tetradecyl-3-tetradecylaminopropionamidine; 14Dea2; TMAG, N-(alpha-trimethylammonioacetyl)didodecyl-D-glutamate chloride; O,O'-ditetradecanoyl-N-(trimethylammonioacetyl) diethanolamine chloride; DOSPER, 1,3-dioleoyloxy-2-(6-carboxy-spermyl)-propylamide; N,N,N',N'-tetramethyl-N,N'-bis(2-hydroxylethyl)-2,3-dioleoyloxy-1,4-butanediammonium iodide; 1-[2-(acyloxy)ethyl]2-alkyl (alkenyl)-3-(2-hydroxyethyl)imidazolinium chloride, derivatives as described by Solodin et al. (1995) Biochem. 43:13537-13544, such as DOTIM, 1-[2-(9(Z)-octadecenoyloxy)ethyl]-2-(8(Z)-heptadecenyl-3-(2-hydroxyethyl)imidazolinium chloride; DPTIM, 1-[2-(hexadecanoyloxy)ethyl]-2-pentadecyl-3-(2-hydroxyethyl)imidazoli nium chloride; 2,3-dialkyloxypropyl quaternary ammonium compound derivatives, contain a hydroxyalkyl moiety on the quaternary amine, as described e.g., Felgner et al. (1994) J. Biol. Chem. 269:2550-2561, such as: DORI, 1,2-dioleoyl-3-dimethyl-hydroxyethyl ammonium bromide; DORIE, 1,2-dioleyloxypropyl-3-dimethyl-hydroxyethyl ammonium bromide; DORIE-HP, 1,2-dioleyloxypropyl-3-dimethyl-hydroxypropyl ammonium bromide; DORIE-HB, 1,2-dioleyloxypropyl-3-dimethyl-hydroxybutyl ammonium bromide; DORIE-HPe, 1,2-dioleyloxypropyl-3-dimethyl-hydroxypentyl ammonium bromide; DMRIE, 1,2-dimyristyloxypropyl-3-dimethyl-hydroxylethyl ammonium bromide; DPRIE, 1,2-dipalmityloxypropyl-3-dimethyl-hydroxyethyl ammonium bromide; DSRIE, 1,2-disteryloxypropyl-3-dimethyl-hydroxyethyl ammonium bromide.

In a preferred embodiment the cationic lipid is selected from a quaternary ammonium compound such as N-[1-(2,3-diacyloxy)propyl]-N,N,N-trimethyl ammonium, which may be present as a salt with a pharmaceutically acceptable counter anion e.g. a chloride, bromide, fluoride, iodide, nitrate, sulfate, methyl sulfate, phosphate, acetate, benzoate, citrate, glutamate or lactate. In an even further preferred embodiment the cationic lipid is DOTAP.

The further amphiphile may be selected from an amphiphile having a neutral or anionic net charge of its hydrophilic moiety (head group). A suitable amphiphile may be selected from sterols or lipids such as phospholipids, lyso-lipids, lysophospholipids, sphingolipids or pegylated lipids, or any combination thereof. A preferred amphiphile is a neutral lipid, sterol or pegylated lipid such as cholesterol, lanosterol, phytosterol, 1,2-diacyl-sn-glycero-3-phosphoethanolamine, including but not limited to dioleoyl (DOPE), 1,2-diacyl-glycero-3-phosphocholines, sphingomyelin. Most preferred the further amphiphile is diacylphosphatidylcholine. Pegylated lipids refer to lipids bearing one or more polyethylene glycol residues.

A suitable aqueous solution according to step a) ii) of the present invention comprises water, optionally a buffer substance and a stabilizing agent and has a pH value between about 3 and 7, preferably between about 4 and about 6.5. Suitable buffer substances are selected from e.g. acetic acid, citric acid, Tris, Bis, phosphatic acid, lactic acid and the like.

The stabilizing agent is preferably selected from a sugar or an alcohol or a combination thereof such as trehalose, maltose, sucrose, glucose, lactose, dextran, mannitol or sorbitol and used in the range of up to about 20% (m/v). Preferably the stabilizing agent is used in the range of about 0.1 (m/v) to about 20% (m/v) and most preferably in the range of about 5 (m/v) to about 15% (m/v) with respect of the total volume of the liposomal dispersion further in step b).

The preparation of a liposomal dispersion according to step b) can be carried out according to several methods well known in the art. In a preferred embodiment of the present invention the film method and in a more preferred embodiment the organic solvent injection method is performed.

According to the film method cationic lipids and optionally amphiphiles and the lipophilic compound are dissolved in an organic solvents or a mixture of different organic solvents that are selected from alcohols (such as ethanol or tert-butanol), halogenated solvents (such as dichloromethane or chloroform) or other suitable organic solvents. After dissolving said compounds in an organic solvent, the organic solvent of the mixture or different organic solvents are evaporated under vacuum to produce a thin film. Instead of producing a thin film from the organic solution containing the cationic lipids, optionally amphiphiles and the lipophilic compound may be dried by lyophilisation or other suitable means so that a homogenous drug-lipid mixture is obtained. An aqueous solution comprising a stabilizing agent is added to rehydrate the lipid film or the dried lipid mixture resulting in a homogeneous dispersion of multilamellar vesicles (MLV).

The organic solvent injection is performed by dissolving cationic lipids and optionally amphiphiles and the lipophilic compound in a water miscible volatile solvent, such as an alcohol or ether, preferably ethanol, and injecting this solution into an aqueous solution comprising a stabilizing agent. The so-called organic phase comprises cationic lipids and optionally amphiphiles and the lipophilic compound and an organic solvent whereby the organic phase should not exceed about 5% (m/v), preferably at least 2.5% (m/v) in the final liquid mixture.

The cationic liposomes of the present invention comprise at least an amount of about 30 mol % cationic lipids, preferably about 40 mol %, more preferably about 50 mol %, even more preferred about 60 mol %, about 70 mol %, about 80 mol %, or about up to 99.9 mol % and are characterized by having a positive zeta potential in about 0.05 M KCl solution at about pH 7.5 at room temperature.

Adjusting the size of liposomes is often performed by sonication in the art. However, in the inventive method homogenising in step c) is preferably performed by extrusion, filtration through membrane filters, high pressure homogenisation and/or high speed homogenization and mostly preferred by extrusion through a membrane with a pore size of about 200 nm under pressure. Membranes with other pore sizes such as 50 nm, 100 nm, 150 nm, 400 nm well known in the art may be used as well. Filtration through membrane filters maybe performed by filtration through membranes composed of PVDF, PES, nylon-filters but also other materials may be used if defined to be suitable. Pore size of membranes shall be in the range of about 200 nm to 450 nm, but pore size is not limited to the sizes mentioned. Different materials and different pore sizes maybe combined in a way to obtain a solution which maybe processed by a sterilizing grade filtration.

For pharmaceutical use, it is a prerequisite that the liposomal formulation can be sterilised through a sterilizing grade filter after the preparation procedure as they are often intended to be used parenterally in a subject in need thereof. Methods for sterilizing liposomes should be destructive for microorganisms, but should not affect physicochemical characteristics of the liposomal formulation in an unfavorable manner. The preferred way for sterilising pharmaceutical products is autoclaving, e.g. at 134° C. for a minimum of 5 min or at 121° C. for a minimum of 15 min. Under these harsh conditions liposomes often show degradation at considerable content, e.g. as agglomeration of liposomes, change of liposomal size or size distribution, hydrolysis/oxidation of lipids, chemical degradation or undesired release of the lipophilic compound from the liposomes. Therefore, sterile filtration and aseptic filling are preferred methods to obtain a pharmaceutical liposomal product for parenteral application. Typically, sterilizing grade filtration is performed once or repeatedly through a membrane with a pore sizes in the range of 0.1 to 0.45 µm. Two to several filters with a defined pore diameter may also be connected in series to achieve a sterilizing grade filtration. Materials commonly used are cellulose derivatives such as cellulose acetate or polyvinyl membranes like PVDF, PES or Nylon but also other materials may be used if defined to be suitable.

Filtration processes may also be used to remove undesired compounds from the liposomal preparation, such as reagents or solvents used in the manufacturing process, or not liposomally loaded lipophilic compound. The pore size of the filter is preferably between the liposomal diameter (typically >60 nm) and the compound to be removed (typically <5 nm). Depending on the size difference ultra filtration (1-1000 kDa molecular weight cut-off) or micro filtration (0.02-1 µm) may be used. Instead of a death end filtration more convenient techniques have been developed like dialysis or cross flow filtration.

A sterilised liposomal preparation can be filled aseptically into appropriate vials, e.g. glass bottles. The filling height of glass bottles is preferred to be in the range of 0.5-10 cm, more preferred in the range of 1.0-5 cm, most preferred in range of 2.0-3.0 cm. Pharmaceutical grade glass bottles maybe in the size of 1 ml to 1000 ml. A liposomal dispersion in an aqueous solution may also be filled into sterile plastic containers or bags.

After step d), dehydration (step e)) is performed. The formulation is dehydrated and reconstituted prior to use with an aqueous solution such as pure water or a solution of a pH-stabilizing agent. The dehydrating process is an important step in the manufacturing process of cationic liposomes since it may directly influence the quality of the dried liposomal preparation and further of the reconstituted liposomal dispersion. Dehydrating can be performed by freeze drying which can be divided into three different steps, (i) freezing, (ii) primary drying, and (iii) secondary drying which are connected by exactly defined temperature/time/pressure ramps.

Freezing of a liposomal dispersion is an important step. It is well known that formation of ice crystals is strongly dependent on freezing speed resulting in different pore sizes of the frozen liposomal dispersion. The drying speed in the following drying steps is mainly influenced by the pore size during freezing.

During primary drying water is removed under vacuum from the frozen dispersion. The temperature of the shelf during freeze-drying as well as the applied vacuum strongly controls the drying process. Choosing an inadequate temperature and pressure may result in several problems during freeze-drying like thawing of the frozen dispersion or phase transition of lipids.

Also during secondary drying a melting of the product may occur. The time of primary drying as well as temperature and pressure of the secondary drying may strongly affect the quality of the liposomal preparation if the parameters are not in a proper range. The quality of the liposomal preparation might be affected as the loaded compound may lack sufficient physical or chemical stability or due to aggregation or crystal formation.

In a preferred embodiment of the present invention dehydrating is performed by freeze-drying. Freezing is preferably performed at atmospheric pressure and the liposomal suspension is frozen to a temperature of about −20 to about −60° C., more preferred to a temperature of about −30° C. to about −50° C. and most preferred to a temperature of about −35° C. to about −45° C. Time is adjusted to ensure complete freezing of the liposomal dispersion and is preferably about 3 to about 10 hours, depending on size, filling height, and type of the glass vessel, wherein the liposomal dispersion is placed.

Freezing and a primary-drying step are connected by a first temperature ramp. The increment of the temperature is determined by the temperature difference during freezing and primary drying. The time of the temperature ramp is preferably in the range of about 0.1 to about 24 hours, more preferably between about 3 to about 5 hours.

Primary drying can be performed at a constant temperature or a temperature ramp may be applied. Drying with a constant temperature is preferably performed at a temperature between about 0° C. and about −50° C., more preferably between about −10° C. and about −30° C. An appropriate vacuum is applied to ensure drying of the product. Vacuum shall be at about 1 mbar to about 0.001 mbar, most preferred at about 0.05 mbar to about 0.15 mbar, dependent on the temperature of the shelf. Also the phase diagram of the formulation has to be taken into consideration for choosing an appropriate vacuum for the primary drying step. The time for the primary drying shall be sufficient to ensure sufficient drying of the liposomal preparation and shall be in the range of about 10 hours to about 200 hours, depending on the lyophilisator.

Primary drying can also be performed using a temperature ramp. The temperature is slowly increased during primary drying. The increase of temperature is preferably in the range of about 0.1 to about 10 K/hour. Temperature can be increased at the beginning or at the end of the primary drying. A pressure rising test can be applied to determine the end of the primary drying.

Primary drying and secondary drying are connected by a second temperature ramp. The increment of the temperature is determined by the temperature at the end of the primary drying and the temperature at the beginning of the secondary drying. The time of the temperature ramp lies preferably in the range of about 0.5 to about 24 hours, more preferably between about 3 to about 5 hours.

Secondary drying can be performed at a constant temperature or a temperature ramp. Drying with a constant temperature is performed at a temperature between about 0° C. and about 50° C., preferably between about 10 and about 20° C., more preferred at about 20° C. An appropriate vacuum is applied to ensure drying of the product. Vacuum shall be at about 1 mbar to about 0.001 mbar, preferably at about 0.1 to about 0.001 mbar. The time for secondary drying shall be sufficient to ensure sufficient drying of the liposomal preparation and should be in the range of about 1 hour to about 50 hours. A pressure rising test can be applied to determine the end of the secondary drying.

Reconstitution behaviour of the dehydrated liposomal preparation such as its reconstitutability, release of the active compound from the liposomal membrane or physicochemical properties of the compound e.g. degradation and the like may be dependent on the dehydrating but also on the reconstitution process. An optimal reconstitution behavior is shown when after adding of an aqueous solution a homogeneous liposomal dispersion is formed. A simple reconstitution protocol is favorable, such as adding the aqueous solution followed by gentle shaking. During reconstitution, dried liposomes are resuspended with water while the physicochemical stability of the lipophilic compound in the liposomal membrane is not jeopardized. Reconstitution behaviour may be examined e.g. by visual assessment, microscopy or light blockage measurements.

The inventive method allows the production of cationic liposomes having a positive zeta potential in about 0.05 M KCl solution at about pH 7.5 at room temperature, preferably having a zeta potential in the range of about 25 mV to 100 mV in about 0.05 M KCl solution at about pH 7.5 at room temperature and more preferably having a zeta potential in the range of about 35 mV to 70 mV in about 0.05 M KCl solution at about pH 7.5 at room temperature.

Further, PI-values of the inventive cationic liposomal preparation are below about 0.6, preferably below about 0.5, more preferred below about 0.4 and most preferred below about 03.

Cationic liposomes prepared by the inventive method and the cationic liposomes disclosed in the present invention have a diameter in the range of about 20 to about 400 nm, preferably about 100 to about 400 nm and more preferably about 200 to about 300 nm.

It is a feature of the present invention that the lipophilic active compound does not substantially partition from the liposomal bilayer and does not substantially form aggregates in an inventive liposomal dispersion in a period of at least 0.5 hours, generally at least 1 hour, preferably at least about 2 hours, more preferably at least about 3 hours and most preferably at least about 4 hours in ambient temperature. A cationic liposome in which the lipophilic active compound does not substantially partition from the liposomal bilayer is one in which generally less than about 20%, usually less than about 10%, usually less than about 5%, typically less than about 1% and preferably less than about 0.5% of the total lipophilic active compound amount loaded in the cationic liposome has partitioned from the liposome bilayer.

Furthermore, the present invention is characterized by a sufficient chemical stability of the lipophilic compound.

BRIEF DESCRIPTION OF DRAWINGS

FIG. 1 discloses liposomal diameter and PI values for LipoPac™ (Batch GB 100).

FIG. 2 discloses liposomal diameter and PI values for LipoPac™ (Batch GB 261).

FIG. 4 discloses particle counts (0-8 h),

FIG. 5 discloses therapeutic efficacy of LipoPac™ vs. Taxotere® in A-375 melanoma in nude mice.

FIG. 6 discloses therapeutic efficacy of LipoPac™ vs. Taxol® in A-375 melanoma in nude mice.

FIG. 7 discloses therapeutic efficacy of LipoPac™ vs. Taxol® in B-16 melanoma in C57/BL6 mice.

FIG. 8 discloses UV-VIS spectra of camptothecin in $CHCl_3$/MeOH stock solution (a), in a 10 mM DOTAP/DOPC liposomal preparation, active compound/lipid ratio 1:1000 (b), and after dissolving a liposomal preparation 1:5 in THF/MeOH/HCl (c).

Figure 3A:
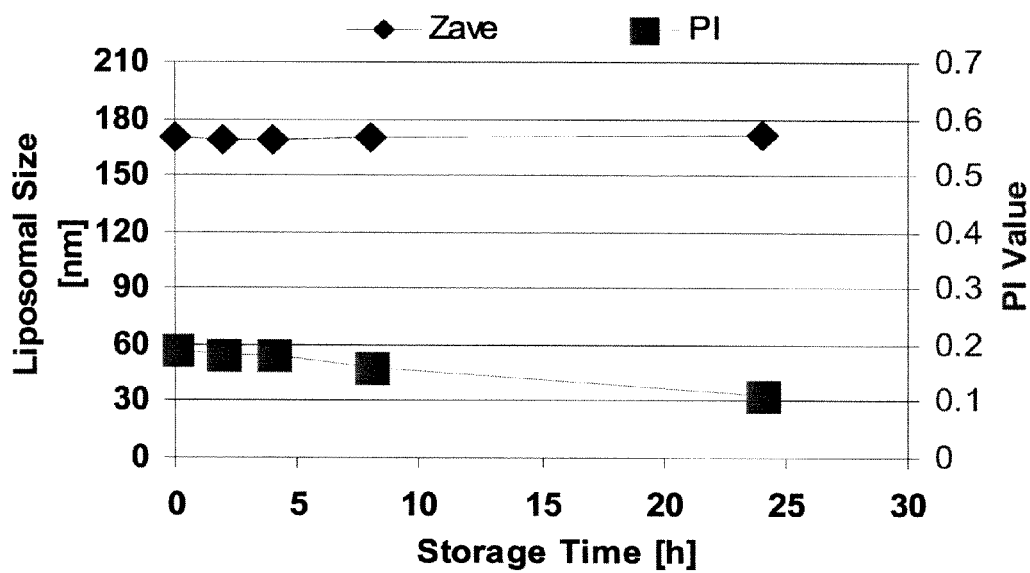
FIGS. 3A-C disclose storage stability as determined by PCS measurements.

Unless defined otherwise, all technical and scientific terms used in this specification shall have the same meaning a commonly understood by persons of ordinary skill in the art to which the present invention pertains.

"About" in the context of amount values refers to an average deviation of maximum +/−20%, preferably +/−10% based on the indicated value. For example, an amount of about 30 mol % cationic lipid refers to 30 mol %+/−6 mol % and preferably 30 mol %+/−3 mol % cationic lipid with respect to the total lipid/amphiphile molarity.

"Amphiphile" refers to a molecule consisting of a water-soluble (hydrophilic) and an organic solvent-soluble (lipophilic) moiety. A suitable amphiphile of the present invention can be cationic, neutral or anionic with regard to the net charge of the hydrophilic moiety (head group). A cationic amphiphile has a positive net charge, a neutral amphiphile a neutral and an anionic amphiphile an anionic net charge. An amphiphile, such as used in the present invention, is selected from sterols such as cholesterol, phytosterol or lanosterol or lipids such as lysophospholipids, sphingolipids or pegylated lipids such as 1,2-diacyl-sn-glycero-3-phosphoethanolamine, including but not limited to dioleoyl (DOPE), 1,2-diacyl-glycero-3-phosphocholines, sphingomyelin. Pegylated lipids refer to lipids bearing one or more polyethylene glycol residues.

"Aqueous solution" refers to any solution comprising water and optionally at least one suitable additive which is completely dissolved in water. Such additives may be buffers or their individual components, sugars, alcohols, stabilizing agents.

"Camptothecin" refers to any camptothecin or derivatives thereof. A camptothecin derivative is obtained from any chemical derivatization of camptothecin. In the sketch of the molecule, the most frequent derivatization sites are outlined as $R_1$-$R_5$. In the table, typical examples for derivatization at the different sites are listed. Any combination of these examples and any other derivatization may be performed. The compound may be present as a hydrochloride. The lactone ring may be seven-membered instead of six-membered.

| Name | R1 | R2 | R3 | R4 | R5 |
|---|---|---|---|---|---|
| camptothecin | H | H | H | H | H |
| 9-Nitro-camptothecin | H | H | $NO_2$ | H | H |
| 9-Amino-camptothecin | H | H | $NH_2$ | H | H |
| 10-Hydroxy-camptothecin | H | OH | H | H | H |
| Topotecan | H | OH | N—$(CH_3)_2$ | H | H |
| SN38 | H | OH | H | $CH_2$—$CH_3$ | H |
| Camptosar® | H | 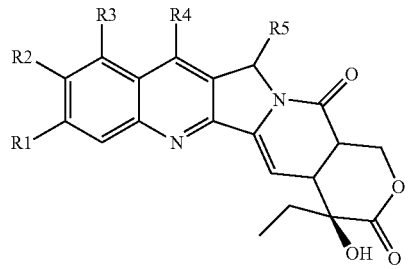 | | H | $CH_2$—$CH_3$ | H |
| Lurtotecan® | R1 and R2 is: O—CH2—CH2—O | | | H | H | H |
| DX-8951f | H | | H | H | H | F |

"Cationic lipid" refers to an amphiphile that has a positive charge (at physiological pH) as measurable by instrumentation utilized at the time of the measurement. Where there are fatty acids or alkyl chains present on the cationic lipid, they could be 12-24 carbons in length, containing up to 6 unsaturations (double bonds), and linked to the backbone by either acyl or ether linkages; there could also only be one fatty acid or alkyl chain linked to the backbone. Where there is more than one fatty acid or alkyl chain linked to the backbone, the fatty acids could be different (asymmetric). Mixed formulations are also possible.

"Cationic liposomes" can be prepared from the cationic lipids themselves, or in admixture with a further amphiphile such as sterols or lipids like cholesterol, phospholipids, lysolipids, lysophospholipids, sphingolipids or pegylated lipids with a negative or neutral net charge, particularly neutral lipids such as cholesterol; 1,2-diacyl-sn-glycero-3-phosphoethanolamines (including but not limited to dioleoyl (DOPE)); 1,2-diacyl-sn-glycero-3-phosphocholines; natural egg yolk or soy bean phosphatidylcholine (PC), and the like; synthetic mono- and diacyl-phosphoethanolamines. Asymmetric fatty acids, both synthetic and natural, and mixed formulations, for the above diacyl derivatives may also be included.

"Cationic liposomal preparation or formulation" refers to either a dehydrated liposomal preparation or formulation or a liposomal dispersion.

"Chemical stability" of the lipophilic compound refers to a significant change of it's original chemical structure, and is defined as about 5% potency change from the initial assay value (original compound), preferably about 2% or appearance of specific degradation products exceeding its acceptance criteria with respect to toxicological limits and safety aspects. For lipophilic compounds such as paclitaxel chemical stability can be defined by HPLC/LC-MS/MS and typically means less than 5% degradation products of said compound. Typical degradation products of paclitaxel are e.g. Baccatinlll, 7-Epi-Taxol etc. (Monography of Paclitaxel, USP26, [January-March 2003], USPC, Inc.).

"Compound loaded into the liposome" or "liposomally loaded compound" or liposomal compound" is used synonymously and refers to a compound that is either integrated in the lipid bilayer of the liposome or associated with the lipid bilayer of the liposome of the liposomal preparation.

"Concentration" of x mol % of an amphiphilic or lipophilic compound refers to the mol fraction of this compound of the total lipid concentration. Concentrations of water soluble compounds are given in % (m/m) or % (m/v) of the total preparation.

"Lipophilic compound" refers to a compound that is characterized by its favorable interaction with the lipophilic part of the liposomal membrane. In liposomal formulations the lipophilic compound is mainly incorporated (embedded) in the membrane or strongly associated with the same. No significant amount is present in the non-liposomal environment, as it would be the case for polar water-soluble compounds.

"Liposomal dispersion" refers to liposomes within an aqueous solution. The term liposomal suspension may also be used in the same sense as "liposomal dispersion" if not otherwise stated.

"Liposomes" refer to microscopic spherical membrane-enclosed vesicles (50-2000 nm diameter) made artificially in the laboratory or production plant. The term "liposome" encompasses any compartment enclosed by a lipid bilayer. Liposomes are also referred to as lipid vesicles. In order to form a liposome the lipid molecules comprise elongated non-polar (hydrophobic) portions and polar (hydrophilic) portions. The hydrophobic and hydrophilic portions of the molecule are preferably positioned at two ends of an elongated molecular structure. When such lipids are dispersed in water they spontaneously form bilayer membranes referred to as lamellae. The lamellae are composed of two mono layer sheets of lipid molecules with their non-polar (hydrophobic) surfaces facing each other and their polar (hydrophilic) surfaces facing the aqueous medium. The membranes formed by the lipids enclose a portion of the aqueous phase in a manner similar to that of a cell membrane enclosing the contents of a cell. Thus, the bilayer of a liposome has similarities to a cell membrane without the protein components present in a cell membrane. As used in connection with the present invention, the term liposome includes multilamellar liposomes, which generally have a diameter in the range of 1 to 10 μm and are comprised of anywhere from two to hundreds of concentric lipid bilayers alternating with layers of an aqueous phase, and also includes unilamellar vesicles which are comprised of a single lipid layer and generally have a diameter in the range of about 20 to about 400 nm, preferably about 100 to about 400 nm, more preferably about 200 to about 300 nm. The vesicles can be produced by subjecting multilamellar liposomes to extrusion under pressure through membranes having pores of defined size, or by high pressure homogenization. Further homogenization methods which are suitable are well known in the art.

"Physical stability" of the lipophilic compound loaded into the liposome refers to the physical state of the compound. The formation of extra-liposomal aggregates (e.g. crystals of the compound) is the most common form of physical instability of a compound. In the case of taxanes, aggregation is visible by the formation of needles of the taxane. Crystallization of a taxane can be measured by visual inspection of liquid liposomal formulation, light microscopy or light blockage measurement or dynamic light scattering. Physical stability of the liposomal dispersion refers also to characteristics such as liposomal size and size distribution or the existence of particles larger than 1 μm. Especially during manufacturing liposomal formulation of a lipophilic compound liposomal characteristics should be maintained.

"Physicochemical stability" refers to a combination of chemical and physical stability.

"PI value" refers to the Polydispersity Index which refers to the particle size distribution in a liposomal dispersion as measured by dynamic light scattering techniques, e.g. with a Malvern Zetasizer 1000 or 3000.

"Stabilizing agent" refers to an agent that stabilizes compound-loaded liposomes during manufacturing to maintain the physicochemical stability of the lipophilic compound and the liposomal formulation. For example for freeze-dried products, cryoprotectants are used as stabilizing agents during manufacturing.

"Taxane" refers to the class of antineoplastic agents having a mechanism of microtubule action and having a structure that includes the unusual taxane ring structure and a stereospecific side chain that is required for cytostatic activity. Taxane further refers to a variety of known taxane derivatives, including both hydrophilic derivatives, and hydrophobic derivatives. Taxane derivatives include, but not limited to, galactose and mannose derivatives described in International Patent Application No. WO 99/18113; piperazino and other derivatives described in WO 99/14209; taxane derivatives described in WO99/09021, WO 98/22451, and U.S. Pat. No. 5,869,680; 6-thio derivatives described in WO 98/28288; sulfenamide derivatives described in U.S. Pat. No. 5,821,263; and paclitaxel derivatives described in U.S. Pat. No. 5,415,869.

"Total lipid concentration" refers to the concentration of the sum of amphiphilic compounds and lipophilic compounds.

"Zeta potential" refers to a surface potential of a particle such as a colloidal particle measured with an instrument such as a Zetasizer 3000 using Laser Doppler micro-electrophoresis under the conditions specified. The zeta potential describes the potential at the boundary between bulk solution and the region of hydrodynamic shear or diffuse layer.

In contrast to the methods disclosed in the art, stability of the loaded active compound during manufacturing steps a) to d) and reconstitution step f) of the present invention is preferably further controlled by any of the following means:
- controlled (low) pH in the aqueous phase
- controlled (low) temperature
- controlled (high) speed of manufacturing and/or application.

The inventive method allows physical and chemical stabilization of the loaded active compound while the liposome is in an aqueous environment.

Limitations of processing liposomes on production scale as methods disclosed in the art as mentioned above partially or generally lack the ability of up-scaling in order to fulfill the requirements which are necessary for market production. With the inventive method the large scale production of physicochemically stable cationic liposomes comprising a lipophilic active compound is disclosed for the first time.

Manufacturing of the cationic liposomes of the present invention, sterile filling and transfer to the freeze-dryer requires 4-18 hours. Afterwards the liposomes are stored e.g. as a freeze-dried powder with a water content of about 0.1 to about 2.5%, preferably about 0.5 to about 1%. Prior to application the freeze-dried powder has to be reconstituted, which means that the liposomes are redispersed in an aqueous solution or water what may lead to physicochemical instability of the liposomal formulation and the loaded lipophilic compound. Therefore, the in-use stability has to cover the time period for reconstitution, transfer to the ward and application to the patient (which is typically several hours) and should cover a minimum of 8 h, ideally 24 h. Thus, the minimum time period for handling the aqueous liposomal preparation is 12 h at refrigerated temperatures (2-8° C.) and additionally 4 h at ambient temperature.

With the present invention a method is provided in which chemical stability of the cationic liposome comprising an active compound is warranted for the depicted time frame.

Thus, in a preferred embodiment of the inventive method said liposomal preparation comprising said active compound is physically and chemically stable in any one of the steps b) to d) or f) for at least 12 hours at about 2° C. to about 8° C. and at least about 4 hours at ambient temperature.

Physical and chemical stability in the context of the present invention relate to the cationic liposome as well as the active compound. Physicochemical stability of the active compound refers to the lipophilic compound which is loaded into the cationic liposome of the liposomal preparation. Loaded means that the compound can be integrated/embedded in the lipid bilayer of the liposome and/or associated inside and/or outside with the liposome.

Physically stable regarding the loaded compound means that e.g. substantially no aggregation products of the compound are detectable. Physical instability is detectable by means of measurement of non visible particles (e.g. by light blockage measurement), light microscopy and dynamic light scattering (DLS). Chemical stability means that degradation products are below about 5% of the total amount of the compound. Detection of degradation products can be performed e.g. by HPLC.

Apart from stability considerations the pH of a pharmaceutical dosage form is determined by its mode of application. In general, for an i.v. application (injection, infusion) solutions at physiological pH are preferred. Therefore, non-buffered aqueous solutions or a physiological buffer in the range of pH 7.0-7.5 are usually used for the manufacturing of paclitaxel liposomes. None of the disclosures dealing with the loading of paclitaxel in cationic liposomes consider the chemical stability of liposomal paclitaxel. Accordingly, the pH is chosen considering a maximum tolerability of the pharmaceutical formulation in the patient, which is at physiological pH.

The ignorance of the stability issue by the most recent paper published on paclitaxel in cationic liposomes (such as temperature and pH, see [3]) is supported by the fact that the manufacturing process is performed at elevated temperature as has been described above.

It is known from the scientific literature that paclitaxel in an aqueous buffer is most stable at an acidic pH in the range 3-5 [4]. Nevertheless, data published for paclitaxel formulated with negatively charged or neutral liposomes differ significantly from findings with positively charged liposomes. Sharma and Straubinger [1] reported for neutral and anionic liposomes a chemical stability of more than 3 months at 4° C. and RT. On the other hand it was found by the applicants that decomposition in cationic formulations may occur on a time scale of hours or days. This shows that the compound-loaded liposomal membranes represent a highly complex system, where interactions between the individual components are critical for the physicochemical stability of paclitaxel-loaded liposomes.

Experiments show that the chemical stability of (phosphoester-)lipids in liposomes is dependent on the pH of the environment (e.g. [5], [7], [8]). Most neutral and anionic liposomes show optimal physicochemical stability at about pH 6.5 and a more or less significant loss of stability with rising or decreasing pH value due to e.g. ester hydrolysis of the lipid structures. Vernooij et. al. show, that these results can not be transferred to cationic liposomes composed of DOTAP and DOPE. In these liposomes the DOTAP and the DOPE are most stable at a pH below 6.4 and 6.1, respectively, and hydrolysis rate in this region is almost independent of pH. The authors failed to explain the observed hydrolysis kinetics on basis of their existing model, but suggested that amine-influenced hydrolysis may play an important role in shaping the k-pH profiles.

However, it is questionable whether one of the above mentioned models applies to a formulation containing another neutral lipid instead of DOPE. The optimum pH for the chemical stability of lipids used for cationic liposome formulations can, therefore, not be concluded from the prior art disclosures.

In the present invention it was surprisingly found that cationic liposomes comprising paclitaxel are characterized by best chemical stability at acidic pH values. This is in sharp contrast to the data published for neutral and/or anionic liposomes ([1], [6]).

Thus, in a preferred embodiment the pH value of the aqueous medium in any one of the steps b) to d) and f) of the inventive method is such that said liposomal preparation maintains physical and chemical stability for at least 12 hours at about 2° C. to about 8° C. and at least about 4 hours at ambient temperature, preferably the pH value is between about 3 and about 7 and more preferably between about 4 and about 6.5.

In another preferred embodiment, the inventive method further comprises cooling to a temperature between about −1° C. and about 15° C., preferably to a temperature between about 1° C. and about 10° C., most preferably between about 2° C. and about 8° C.

The invention further provides a method for producing a cationic liposomal preparation comprising a taxane as anti-angiogenic and cytotoxic agent. Such preparation may inhibit angiogenesis and is thus useful in the treatment of a variety of diseases such as cancer, chronic inflammation and the like.

Thus, another object of the present invention is to provide a method for producing a cationic liposomal preparation comprising at least one amphiphile selected from cationic lipids in an amount of at least about 30 mol %, optionally at least one further amphiphile in an amount of up to about 68 mol %, a taxane in an amount of at least about 2 mol % and a stabilizing agent in an amount of about 0.1% (m/v) to about 20% (m/v),
comprising the steps of
 a) providing
  i. an organic solution comprising an organic solvent, said taxane and said cationic lipid, and optionally said further amphiphile,
  ii. an aqueous solution comprising said stabilizing agent,
 b) preparing a cationic liposomal preparation from said solution a) i) and a) ii), wherein said preparation comprises cationic liposomes in an aqueous medium,
 c) optionally homogenising said preparation at least once and/or
 d) optionally sterile filtrating said preparation,
 e) dehydrating said preparation and
 f) optionally reconstituting said cationic liposomes of step e) in an aqueous solution and wherein optionally before step c) and/or d) an ultrafiltration step is included.

In a preferred embodiment of the inventive method said liposomal preparation comprising said taxane is physically and chemically stable in any one of the steps b) to d) or f) for at least 12 hours at about 2 to about 8° C. and at least about 4 hours at ambient temperature.

Generally, the proportion of a taxane in the cationic liposomal preparation of the present invention is less than about 20 mol %. In some embodiments, the cationic liposomal preparation comprises a taxane in a proportion from about 0.5 mol % to about 20 mol %, preferably from about 2 mol % to about 15 mol %. In other embodiments, a taxane is present in about 1 mol % to about 5 mol %, and in still other embodiments from about 5 mol % to about 15 mol % and more preferably from about 10 mol % to about 13 mol %.

In a preferred embodiment of the inventive method said liposomal preparation comprises a taxane, preferably paclitaxel or docetaxel or a lipophilic derivative thereof in an amount of about 1 mol % to about 20 mol %, preferably in an amount of about 2 mol % to about 5 mol % for paclitaxel or preferably in an amount of at least 3 mol % for docetaxel or succinyl-paclitaxel and most preferably in an amount of at least 5 mol % for docetaxel or succinyl-paclitaxel.

It is a feature of the present invention that the taxane does not substantially partition from the liposomal bilayer into the aqueous phase and does not substantially form taxane crystals in a liposomal dispersion in a period of at least 0.5 hours, generally at least 1 hour, preferably at least about 2 hours, more preferably at least about 3 hours and most preferably at least about 4 hours in ambient temperature. A cationic liposome in which the taxane does not substantially partition from the liposomal bilayer is one in which generally less than about 20%, usually less than about 10%, usually less than about 5%, typically less than about 1% and preferably less than about 0.5% of the total taxane amount loaded in the cationic liposome has partitioned from the liposome bilayer.

Yet another object of the present invention is to provide a cationic liposomal preparation obtainable by a process of disclosed method.

Another object of the present invention is to provide a cationic liposomal preparation comprising at least one amphiphile selected from cationic lipids of at least about 30 mol %, optionally at least one further amphiphile of up to about 69.9 mol %, a lipophilic active compound of at least about 0.1 mol % and a stabilizing agent of about 0.1% to about 20% (m/v), characterized in that said liposomal preparation is physically and chemically stable in an aqueous solution for at least 12 hours at 2 to 8° C. and at least 4 hours at ambient temperature.

In a further preferred embodiment of the preparation of the present invention the lipophilic active compound is selected from a taxane, a camptothecin, a statin, a depsipeptide, thalidomide, other agents interacting with microtubuli such as discodermolide, laulimalide, isolaulimalide, eleutherobin, Sarcodictyin A and B and in a more preferred embodiment the lipophilic active compound is selected from paclitaxel, docetaxel, camptothecin or any lipophilic derivative thereof.

In a preferred embodiment of the present invention said liposomal preparation comprises a taxane, preferably paclitaxel or docetaxel or a lipophilic derivative thereof in an amount of about 1 to about 20 mol %, preferably in an amount of about 5 mol % for paclitaxel or preferably in an amount of at least 5 mol % for docetaxel or succinyl-paclitaxel. In a further preferred embodiment said liposomal preparation comprises camptothecin lactone in an amount of about 0.1 mol % to about 1 mol %.

In a preferred embodiment the inventive preparation comprises a stabilizing agent such as trehalose in the range of about 5% (m/v) to about 15% (m/v) with respect to the total volume of the preparation.

Yet another object of the present invention is to provide a cationic liposomal preparation comprising at least one amphiphile selected from cationic lipids of at least about 30 mol %, optionally at least one further amphiphile of up to about 65 mol %, paclitaxel of about 5 mol % and a stabilizing agent of about 0.1% (m/v) to about 20% (m/v), characterized in that said liposomal preparation is physically and chemically stable in an aqueous solution for at least 12 hours at 2° C. to 8° C. and at least 4 hours at ambient temperature.

It is a further object of the present invention to provide a cationic liposomal preparation comprising at least one amphiphile selected from cationic lipids of at least about 30 mol %, optionally at least one further amphiphile of up to about 65 mol %, docetaxel of at least about 5 mol % and a stabilizing agent of about 0.1% (m/v) to about 20% (m/v).

Another object of the present invention is to provide a cationic liposomal preparation comprising at least one cationic lipid of at least about 30 mol %, optionally at least one further amphiphile of up to about 65 mol %, succinyl-paclitaxel of at least about 5 mol % and a stabilizing agent of about 01% (m/v) to about 20% (m/v).

It is a feature of the present invention that the cationic liposomes have a positive zeta potential in about 0.05 M KCl solution at about pH 7.5 at room temperature, preferably a zeta potential in the range of about 25 mV to 100 mV in about 0.05 M KCl solution at about pH 7.5 at room temperature and more preferably a zeta potential in the range of about 35 mV to 70 mV in about 0.05 M KCl solution at about pH 7.5 at room temperature.

A further feature of the present invention is that any inventive liposomal preparation comprises liposomes with an average particle size of about 50 nm to about 400 nm, preferably about 100 nm to about 300 nm.

The pharmaceutical composition of the present invention can be in a dry, lyophilized form or in the form of a liquid suspension. The lyophilized form is preferred, because it can be stably stored for periods up to several months or years. Suspensions of the pharmaceutical composition of the present invention in low acidic pH (buffered or acidified) are stable for periods of hours up to months, depending upon the temperature, compound content, and phospholipid constituents.

Another object of the present invention is to provide a pharmaceutical composition comprising any one of the inventive liposomal preparations together with a pharmaceutically acceptable carrier, diluent and/or adjuvant.

The pharmaceutical composition of the present invention is active in the field of cancer treatment, wound healing as well as several chronic diseases, and in general in the treatment of diseases associated with enhanced angiogenic activity by administering the composition to patients in an effective amount. The liposomes of the present invention may be administered alone or in combination with suitable pharmaceutical carriers or diluents. Suitable application forms are parenteral routes of administration such as intramuscular, intravenous, intraperitoneal as well as subcutaneous administration. Dosage forms suitable for parenteral administration include solutions, suspensions, dispersions, emulsions and the like well known in the art.

In light of the foregoing general discussion, the specific examples presented below are illustrative only and are not intended to limit the scope of the invention. Other generic and specific configurations will be apparent to those persons skilled in the art.

EXAMPLES

1. Example 1

Preparation of Paclitaxel Loaded Liposomes (LipoPac™)

The following example describes manufacturing of paclitaxel loaded liposomes (LipoPac™) which is applicable to a scale of 4 l, 12 l and at least 66 l. All liquid formulations are stoichiometrically composed of

| | |
|---|---|
| DOTAP-Cl | 50 mol % |
| DOPC | 47 mol % |
| paclitaxel | 3 mol % |
| trehalose-dihydrate | 108.2 g/l |
| ethanol | 1.33% (m/m) |

Ethanol is an intermediate product. It is proposed that ethanol is at least partially removed by lyophilisation. Residual amounts of ethanol were determined for Protocol 2 and 3 and found to be below 1%.

1.1 Ethanolic Lipid Solution

An appropriate amount of DOTAP-Cl, DOPC and paclitaxel is dissolved in ethanol to give a final concentration of 400 mM of total lipophilic compounds in ethanol. A clear solution was obtained (ethanolic lipid solution). The ethanolic lipid solution maybe stored overnight at 2-8° C.

1.2 Preparation of Trehalose Solution

An appropriate amount of trehalose-dihydrate is dissolved in water for injection (WfI) and stirred for at least 5 min until a clear solution is obtained.

The prepared solution is filtered through a 0.22 μm PVDF (Millipak) flat filter membrane at ambient temperature. Alternatively, the trehalose solution maybe filtered through a 022 μm Celluloseacetate membrane (Sartobran® P) at ambient temperature or through a sterilizing grade sterile filtration membrane (0.22 μm) at ambient temperature. Before starting the ethanol injection pH and temperature are adjusted to pH 3-7 and 2-8° C. respectively and maintained at this temperature.

1.3 Ethanol Injection

Ethanol lipid solution is injected into stirred trehalose solution with a speed of at least 0.433 ml/min but can be enhanced accordingly. Trehalose solution is stirred with a speed of at least 280 rpm but can be enhanced accordingly. Injection is performed with a drop funnel or through a capillary using a piston pump. The obtained raw dispersion is stirred for at least 5 min.

1.4 Extrusion

The raw dispersion is extruded fivefold through a 200 nm polycarbonate membrane. The liposomal dispersion is forced five times through the membrane applying a pressure of at least 2 bar. During the extrusion, temperature is maintained at 2-8° C.

1.5 Sterile Filtration

After extrusion the liposomal dispersion is filtered through a sterilizing grade filter (Millipak 200, 0.22 μm). A pressure of at least 2.5 bar is applied at once. Sterile filtration is performed at 2-8° C. A second sterile filtration step maybe performed to ensure complete removal of bacteria.

1.6 Freeze-Drying

Freeze-drying has to be adjusted to the size of the certain preparation scale resulting in similar preparations.

Protocol 1 for a 4 l Scale, 6 R-Vials with a Filling Volume of 2, 1 ml/Vial:

Freeze-drying is performed using a Christ freeze-dryer (Epsilon 2-12D). Briefly, samples are frozen at −40° C. for 3 hours. Primary drying was performed at −40° C., −30° C. and −16° C. Pressure was set to 0.1 mbar. Secondary Drying was performed at +20° C. and a vacuum was applied (0.01 mbar). Vials are closed at approx. 800 mbar of pressure under nitrogen.

Protocol 2 for a 12 l Scale, 50 H-Vials with a Filling Volume of 14 ml/Vial:

Freeze-drying is performed using a Christ freeze-dryer. Briefly, samples are frozen at −30° C. for 3 h. After freezing, temperature and pressure are adjusted to −16° C. and 0.1 mbar. After 60 h of primary drying, temperature is increased to +20° C. and pressure is decreased to 0.001 mbar within 3 h. Secondary drying is performed for 12 h at +20° C. and 0.001 mbar. Vials are closed at approx. 800 mbar of pressure under nitrogen.

Protocol 3 for a 66 l Scale, 100 H-Vials with a Filling Volume of 25 ml/Vial:

Freeze-drying is performed using a Kniese EK-10 freeze-dryer. Briefly, samples are frozen at −40° C. for at least 3 h. After freezing, temperature of product is increased to −16° C. Pressure is adjusted to 0.1 mbar. After 12 h of primary drying, temperature is increased to 0° C. within 59 h. Secondary drying is performed for 12 h at +20° C. and 0.01 mbar using a ramp of 3 h to adjust pressure and temperature. Vials are closed at approx. 800 mbar of pressure under nitrogen.

Protocol 4 for a 66 l Scale, 100 H-Vials with a Filling Volume of 25 ml/Vial:

Freeze-drying is performed using a Kniese EK-10 freeze-dryer. Briefly, samples are frozen at −40° C. for at least 3 h. After freezing, temperature of product is increased to −16° C. Pressure is adjusted to 0.1 mbar. Temperature and pressure are kept constant for a time period of 60 to 100 h. Secondary drying is performed for 12 h at +20° C. and 0.01 mbar using a ramp of 3 h to adjust pressure and temperature. Vials are closed at approx. 800 mbar of pressure under nitrogen.

LipoPac™ was manufactured according to the procedure described above. All preparations were homogenous in size (Zave and PI) after extrusion and sterile filtration (Zave about 220 nm and PI about 0.2-0.3. After lyophilisation. samples were obtained with a PI-index of 0.27 (batch GB100 FIG. 1) resp. 0.56 (GB261 FIG. 2), depending on the lyophilisation protocol which was used.

GB100 has been manufactured according to a lyophilisation protocol similar to protocol 4 whereas GB261 has been manufactured according to a lyophilisation protocol similar to protocol 3.

HPLC analysis of different batches were made with focus on paclitaxel degradation as it is observable by the formation of 7-epitaxol, one major degradation product. Results are shown in Table 1.

TABLE 1

Formation of 7-epitaxol in different batches.

| Batch | Temperature during manufacturing | 7-Epitaxol |
|---|---|---|
| 1 | room temperature | 1.5% |
| 2 | | 1.2% |
| 3 | | 0.9% |
| 4 | 2-8 °C. | 0.4% |
| 5 | | 0.2% |
| 6 | | 0.3% |
| 7 | | 0.7% |
| 8 | | 0.7% |
| 9 | | 0.5% |

Formation of 7-epitaxol is dependent on temperature of manufacturing of bulk material. Batches 1-3 were manufactured at room temperature in 8-121 scale. 7-Epitaxol was found to be in the range of 0.9-1.5%. Decreasing manufacturing temperature to 2-8° C. resulted in a decrease of 7-epitaxol-content to 0.2-0.7%. The pH of all liposome suspensions during manufacturing was between 4.7 and 6.

2. Example 2

Influence of the pH Value on the In-Use Stability of Liposomal Paclitaxel after Reconstitution 2.1 Summary Objective of this study was to determine the influence of temperature and pH-value on the in-use stability of liposomal paclitaxel after reconstitution of lyophylized preparations. Studies were performed with different samples of liposomal paclitaxel, batch Si 175 at two different temperatures and seven different pH values (pH 5.0 to 8.0).

Freeze-dried samples of liposomal paclitaxel batch Si175 (prepared as disclosed above in Example 1) were reconstituted in 10 mM BISTRIS or TRIS buffer solutions, which were adjusted to pH values in the range of 5.0 to 8.0 before. The aqueous dispersions were stored either at room temperature or in a refrigerator (2-8° C.) for up to 32 h.

Room Temperature:

The degradation of the liposomal paclitaxel strongly depends on the pH value of the aqueous dispersion. paclitaxel is stable at pH values at and below 6.0 for up to 32 h. Only about 1% of the active substance degraded during 32 h at pH 6.0. At higher pH values the degradation increased dramatically from about 8% at pH 6.5 to about 70% at pH 8.0 within 32 h.

The main degradation product was 7-epi-taxol. Its amount formed during 32 h increased from about 1% at pH 6.0 to about 25% at pH 8.0. Baccatin III and 10-deacethyltaxol linearly increased to about 12% after 32 h at pH 8.0.

An acceptable in-use stability of not more than 2% degradation of liposomal paclitaxel at room temperature could only be achieved if the pH value of the aqueous solution is at or below 6.0. Then, the formation of degradation compounds could nearly be neglected. An in-use stability of 12 h could be achieved without problems in this pH range. Above pH values of 6.0, the in-use stability of 12 h has to be reduced and adjusted according to the amounts of degradation products accepted in the dispersion.

Refrigerator:

The degradation of liposomal paclitaxel could be significantly slowed down at lower temperatures. Paclitaxel is stable at pH values at or below 6.5. That means, that the critical pH value could be increased from 6.0 to 6.5 compared to the experiments conducted at room temperature. At higher pH values degradation increased, but to smaller degrees than at room temperature. At pH 8.0 more than twice the amounts of paclitaxel could be recovered after 32 h.

Degradation products were formed in the same proportions as in the experiments conducted under room temperature but in significantly lower quantities. Again, 7-epi-taxol was the main degradation product of paclitaxel (10% at pH 8.0). Baccatin III and 10-deacethyltaxol were formed for about 5 to 6% at pH 8.0. Found unknown substances were the same.

The in-use stability of liposomal paclitaxel could be significantly improved at lower temperatures (2-8° C.). In a pH range of 5.0 to 6.5, reconstituted samples can be stored for up to 32 h without the formation of degradation products. The degradation is much slower compared to room temperature even at higher pH values.

These experiments demonstrated, that storage of liposomal paclitaxel in an acidic medium (pH below 6.5) in the refrigerator reduced the degradation processes of the active substance paclitaxel. The in-use stability of the dispersions could be extended to more than 12 h under these conditions.

2.2 Experimental 2.2.1 Test System—Formulation

A liposomal paclitaxel formulation as shown in Table 2 was used in this study:

TABLE 2

Investigated liposome formulation

| Formulation | Batch No. | Theoretical Composition [mM] | | | Volume Lyophilisate per Vial [mL] |
|---|---|---|---|---|---|
| | | DOTAP | DOPC | Paclitaxel | |
| Liposomal paclitaxel | Si 175 | 5.0 | 4.7 | 0.3 | 2.1 |

2.2.2 Instruments

HPLC-System:
 Autoinjector: SIL-10ADVP with sample rack No. 11
 Isocratic pump: LC-10ADVP
 Degasser: DGU-14A
 Column oven: CTO-10ASVP
 DAD Detector: SPD-M10AVP
 Controller: SCL-10AVP Software for evaluation: CLASS VP Version 6.10 Shimadzu Deutschland GmbH; 47269 Duisburg, Germany pH-Meter:
  InoLab pH Level 2; WTW GmbH and Co. KG; 82362 Weilheim, Germany Refrigerator and freezer commonly available in the laboratory.

2.2.3 HPLC Method

Columns:
  LiChroCART® 250-4, LiChrospher® 60, RP-select B, length 250 mm,
  ID: 4 mm, particle size: 5 μm; Order No.: 1.50839.0001
Pre-Column: e.g. 8/4 LiChrospher® 100-5 C18; Order No. 1-50957 Merck KgaA, 64293 Darmstadt, Germany
Injection Volume: 10 μL
Oven Temperature: 35° C.
Mobile Phase: acetonitrile/THF/2 mM ammonium acetate (32/12/56, v/v/v; v=Vol %)
Flow Rate: 1.00 mL/min
Detector Wavelength: 229 nm 2.2.4 Preparation of Samples The lyophilized samples (preparation described in Example) were reconstituted in 10 mM BISTRIS or TRIS buffer solutions, which were adjusted to pH values in the range of 5.0 to 8.0 with hydrochloric acid. The solutions were carefully shaken until a homogeneous, slightly turbid dispersion was obtained, which was free of visibles particles. The solutions were used 30 min after preparation earliest.

Preparation of the 10 Mm BISTRIS Buffer Solutions:

About 1.26 g of BISTRIS were weighed into a 1000 mL beaker and diluted with 600 mL of water (Aqua ad inject., exactly measured with a graduated cylinder). Then, five 100 mL aliquots of this solution were adjusted with 1 M hydrochloric acid (HCl) to pH values of 5.0, 5.5, 6.0, 6.5 and 7.0. About 0.5 mL (pH 7.0) to 4.0 mL (pH 5.0) of the acid were needed for the adjustment of the pH values. The 1 M HCl was prepared by dilution of about 9 g HCl (37%) with 100 mL of water (Aqua ad inject.).

The buffer capacity of the BISTRIS buffer at pH values below 5.5 is low and can be neglected at a pH value of 5.0. Nevertheless it was chosen, because most buffers could not be used in combination with cationic liposomes.

Preparation of the Tris Buffer Solutions:

About 1.21 g of TRIS were weighed into a 1000 mL volumetric flask and filled to volume with water (Aqua ad inject.). Then, two 100 mL aliquots of this solution were adjusted with 1 M HCl to pH values of 7.5 and 8.0. About 1 mL (pH 8.0) and 1.5 mL (pH 7.5) of the acid were needed.

2.2.5 Storage Conditions and Sampling Schedule

After preparation, samples were stored as described in Table 3. Sampling was done after 0, 1, 3, 6, 8, 24 and 32 h after reconstitution. At each sampling interval, 200 μL aliquots of the dispersion were taken out of the vial and the parameters purity and content of paclitaxel were determined via HPLC analysis. Additionally, the pH value of the dispersion was determined at each sampling date.

TABLE 3

Storage Conditions

| sample No. | pH value | temperature [° C.] | max. storage time [h] |
| --- | --- | --- | --- |
| 001 | 5.0 | 2-8° C. | 34 |
| 002 | 5.5 | | |
| 003 | 6.0 | | |
| 004 | 6.5 | | |
| 005 | 7.0 | | |
| 006 | 7.5 | | |

TABLE 3-continued

Storage Conditions

| sample No. | pH value | temperature [° C.] | max. storage time [h] |
| --- | --- | --- | --- |
| 007 | 8.0 | | |
| 008 | 5.0 | Room temperature | 34 |
| 009 | 5.5 | | |
| 010 | 6.0 | | |
| 011 | 6.5 | | |
| 012 | 7.0 | | |
| 013 | 7.5 | | |
| 014 | 8.0 | | |

2.3 Results and Discussion 2.3.1 Degradation of Liposomal Paclitaxel at Room Temperature The degradation of liposomal paclitaxel strongly depends on the pH value of the aqueous solution after reconstitution. As can be seen in Table 4, paclitaxel is chemically stable at pH values at and below 6.0 for up to 32 h. Only about 1% of the active substance degraded during 32 h at pH 6.0. Observable degradation of paclitaxel starts at pH values above 6.0 (see Table 6 and Table 7). At pH 6.5 about 10% of the active substance degraded during 32 h. By increasing the pH value from 7.0 to 8.0, the amount of degradation products increased dramatically (see Table 8). At pH 8.0 only about 30% of the original amount of paclitaxel could be recovered. Even in the first sample (0 h) at pH 8.0, 10% of paclitaxel already degraded, because first sampling was done half an hour after reconstitution of the vial.

An acceptable in-use stability of paclitaxel loaded liposomes at room temperature could only be achieved, if the pH value of the aqueous solution is at or below 6.0. Then, the formation of degradation compounds could nearly be neglected. An in-use stability of 12 h could be achieved without problems in this pH range.

Above pH values of 6.0, the in-use stability of 12 h has to be reduced and adjusted according to the amounts of degradation products accepted in the dispersion.

The main degradation product observed in this study was 7-epi-taxol. Its amounts formed during 32 hours increased from about 1% at pH 6.0 to about 25% at pH 8.0. Baccatin III and 10-deacethyltaxol linearly increased to about 12% after 32 h at pH 8.0 (see Table 6, Table 7 and Table 8).

TABLE 4

Influence of storage time and pH on degradation at room temperature.

| | Total Degradation Product [Area %] | | | Absolute |
| --- | --- | --- | --- | --- |
| pH Value | After 0 h | After 8 h | After 32 h | Difference |
| 5.0 | 3.4 | 3.4 | 2.8 | −0.6 |
| 5.5 | 3.3 | 3.3 | 3.4 | +0.1 |
| 6.0 | 3.4 | 3.8 | 4.5 | +1.1 |
| 6.5 | 3.6 | 5.4 | 9.4 | +5.8 |
| 7.0 | 4.3 | 12.9 | 27.1 | +22.8 |
| 7.5 | 5.1 | 16.7 | 35.6 | +30.5 |
| 8.0 | 9.6 | 40.2 | 56.9 | +46.5 |

2.3.2 Degradation of Liposomal Paclitaxel at 2-8° C.

The degradation of liposomal paclitaxel could be slowed down at lower temperatures. As can be seen in Table 5, paclitaxel is stable at pH values ≤6.5. That means, that the critical pH value could be increased from 6.0 to 6.5 compared to room temperature. In the range of pH 5.0 to 6.5 the aqueous system is stable (see also Table 9 and Table 10).

Decomposition starts at pH values above 6.5. At pH 7.0 about 7% of the active substance degraded during 32 h. At higher pH values, degradation increased, but to a smaller degree compared to the experiments conducted at room temperature (see Table 10 and Table 11). At pH 8.0 more than twice the amounts of paclitaxel (30% at rt vs. 64% at 2-8° C.) could be recovered after 32 h.

The in-use stability of liposomal paclitaxel could be significantly improved at lower temperatures (2-8° C.). In a pH range of 5.0 to 6.5, reconstituted samples can be stored for up to 32 h without the formation of degradation products. The degradation is much slower compared to room temperature even at higher pH values. Above pH values of 6.5, the in-use stability has to be adjusted according to the amounts of degradation products accepted in the dispersion.

Degradation products were formed in the same proportions as in the experiments conducted under room temperature but in significantly lower quantities. Again, 7-epi-taxol was the main degradation product of paclitaxel. Its amounts formed during 32 h increased from about 3% at pH 7.0 to about 10% at pH 8.0 (see Table 11). Baccatin III and 10-deacethyltaxol were formed for about 5 to 6% at pH 8.0.

TABLE 5

Influence of storage time and pH on degradation at 2-8° C.

| pH Value | Total Degradation Product [Area %] | | | Absolute Difference |
|---|---|---|---|---|
| | After 0 h | After 8 h | After 32 h | |
| 5.0 | 3.3 | 3.0 | 2.9 | −0.4 |
| 5.5 | 3.2 | 3.0 | 2.8 | −0.4 |
| 6.0 | 3.3 | 3.1 | 3.1 | −0.2 |
| 6.5 | 3.5 | 3.7 | 3.9 | +0.4 |
| 7.0 | 4.4 | 6.7 | 10.0 | +5.6 |
| 7.5 | 5.3 | 10.3 | 12.8 | +7.5 |
| 8.0 | 10.2 | 25.0 | 31.8 | +21.6 |

The same unknown substances were found as in the experiments conducted at room temperature, albeit in much smaller quantities.

2.3.3 Raw Data

TABLE 6

Degradation of liposomal paclitaxel and formation of degradation products at pH 5.0, 5.5 and 6.0 at room temperature (data presented in area %)

| Room Temperature | Time [h] | Baccatin | 10-Deacethyl-taxol | Paclitaxel | 7-Epi-Taxol | unknown 1 | unknown 2 | unknown 3 | Total Degradation Products |
|---|---|---|---|---|---|---|---|---|---|
| pH 5.0 | 0 | 0.34 | 0.59 | 96.6 | 2.5 | 0* | 0 | 0 | 3.4 |
| | 1 | 0.33 | 0.56 | 96.9 | 2.3 | 0* | 0 | 0 | 3.2 |
| | 3 | 0* | 0.47 | 96.9 | 2.7 | 0* | 0 | 0 | 3.2 |
| | 6 | 0.39 | 0.52 | 96.7 | 2.4 | 0* | 0 | 0 | 3.3 |
| | 8 | 0.38 | 0.52 | 96.7 | 2.5 | 0* | 0 | 0 | 3.4 |
| | 24 | 0* | 0.55 | 95.3 | 2.4 | 1.7 | 0 | 0 | 2.9 |
| | 32 | 0.37 | 0* | 97.2 | 2.4 | 0* | 0 | 0 | 2.8 |
| pH 5.5 | 0 | 0.35 | 0.59 | 96.7 | 2.3 | 0* | 0 | 0 | 3.3 |
| | 1 | 0.37 | 0.59 | 96.7 | 2.4 | 0* | 0 | 0 | 3.3 |
| | 3 | 0* | 0.51 | 96.9 | 2.6 | 0* | 0 | 0 | 3.1 |
| | 6 | 0.41 | 0.61 | 96.6 | 2.4 | 0* | 0 | 0 | 3.4 |
| | 8 | 0.37 | 0.54 | 96.7 | 2.4 | 0* | 0 | 0 | 3.3 |
| | 24 | 0* | 0.57 | 94.3 | 2.6 | 2.5 | 0 | 0 | 3.2 |
| | 32 | 0.44 | 0* | 96.6 | 2.9 | 0* | 0 | 0 | 3.4 |
| pH 6.0 | 0 | 0.29 | 0.62 | 96.6 | 2.5 | 0* | 0 | 0 | 3.4 |
| | 1 | 0.38 | 0.67 | 96.4 | 2.5 | 0* | 0 | 0 | 3.6 |
| | 3 | 0* | 0.52 | 96.8 | 2.7 | 0* | 0 | 0 | 3.2 |
| | 6 | 0.43 | 0.69 | 96.4 | 2.5 | 0* | 0 | 0 | 3.7 |
| | 8 | 0.43 | 0.65 | 96.2 | 2.7 | 0* | 0 | 0 | 3.8 |
| | 24 | 0* | 0.80 | 94.0 | 3.3 | 1.9 | 0 | 0 | 4.1 |
| | 32 | 0.64 | 0* | 95.5 | 3.9 | 0* | 0 | 0 | 4.5 |

*the corresponding peaks could not be evaluated due to interferences with the BISTRIS buffer; the area % of the total degradation products were calculated without the compound Unknown 1, as it is most probably not a metabolite of paclitaxel.

TABLE 7

Degradation of liposomal paclitaxel and formation of degradation products at pH 6.5 and 7.0 at room temperature (data presented in area %)

| Room Temperature | Time [h] | Baccatin | 10-Deacethyl-taxol | Paclitaxel | 7-Epi-Taxol | unknown 1 | unknown 2 | unknown 3 | Total Degradation Products |
|---|---|---|---|---|---|---|---|---|---|
| pH 6.5 | 0 | 0.37 | 0.64 | 96.4 | 2.5 | 0* | 0 | 0 | 3.6 |
| | 1 | 0.36 | 0.72 | 96.1 | 2.8 | 0* | 0 | 0 | 3.9 |
| | 3 | 0* | 0.65 | 96.0 | 3.4 | 0* | 0 | 0 | 4.0 |
| | 6 | 0.59 | 0.87 | 95.1 | 3.5 | 0* | 0 | 0 | 4.9 |
| | 8 | 0.64 | 1.0 | 94.6 | 3.8 | 0* | 0 | 0 | 5.4 |
| | 24 | 0* | 1.6 | 90.1 | 6.2 | 2.1 | 0 | 0 | 7.8 |
| | 32 | 0* | 1.8 | 88.1 | 7.6 | 2.5 | 0 | 0 | 9.4 |
| pH 7.0 | 0 | 0.48 | 0.78 | 95.7 | 3.0 | 0* | 0 | 0 | 4.3 |
| | 1 | 0.66 | 1.0 | 94.6 | 3.7 | 0* | 0 | 0 | 5.4 |
| | 3 | 0* | 1.3 | 93.1 | 5.6 | 0* | 0 | 0 | 6.9 |
| | 6 | 1.3 | 2.0 | 89.1 | 7.6 | 0* | 0 | 0 | 10.9 |

TABLE 7-continued

Degradation of liposomal paclitaxel and formation of degradation products at pH 6.5 and 7.0 at room temperature (data presented in area %)

| Room Temperature | Time [h] | Baccatin | 10-Deacethyl-taxol | Paclitaxel | 7-Epi-Taxol | unknown 1 | unknown 2 | unknown 3 | Total Degradation Products |
|---|---|---|---|---|---|---|---|---|---|
| | 8 | 1.5 | 2.4 | 87.1 | 9.0 | 0* | 0 | 0 | 12.9 |
| | 24 | 4.0 | 4.5 | 69.7 | 16.9 | 4.0 | 1.0 | 0 | 26.4 |
| | 32 | 0* | 4.8 | 67.1 | 20.8 | 4.8 | 1.5 | 0 | 27.1 |

*the corresponding peaks could not be evaluated due to interferences with the BISTRIS buffer; the area % of the total degradation products were calculated without the compound Unknown 1, as it is most probably not a metabolite of paclitaxel.

TABLE 8

Degradation of liposomal paclitaxel and formation of degradation products at pH 7.5 and 8.0 at room temperature (data presented in area %)

| Room Temperature | Time [h] | Baccatin | 10-Deacethyl-taxol | Paclitaxel | 7-Epi-Taxol | unknown 1 | unknown 2 | unknown 3 | Total Degradation Products |
|---|---|---|---|---|---|---|---|---|---|
| pH 7.5 | 0 | 0.61 | 0.93 | 94.1 | 3.5 | 0.80 | 0 | 0 | 5.1 |
| | 1 | 0.81 | 1.3 | 92.1 | 5.1 | 0.66 | 0 | 0 | 7.2 |
| | 3 | 0.93 | 1.8 | 88.8 | 7.2 | 1.4 | 0 | 0 | 9.9 |
| | 6 | 1.9 | 2.5 | 84.5 | 9.7 | 1.5 | 0 | 0 | 14.1 |
| | 8 | 2.2 | 3.0 | 81.2 | 11.2 | 2.0 | 0.46 | 0 | 16.7 |
| | 24 | 4.4 | 5.1 | 65.7 | 19.6 | 3.8 | 1.4 | 0 | 30.4 |
| | 32 | 5.2 | 6.7 | 59.6 | 22.1 | 4.8 | 1.7 | 0 | 35.6 |
| pH 8.0 | 0 | 1.2 | 1.8 | 89.4 | 6.6 | 1.1 | 0 | 0 | 9.6 |
| | 1 | 2.0 | 2.9 | 83.3 | 10.7 | 1.1 | 0 | 0 | 15.6 |
| | 3 | 2.6 | 4.4 | 73.0 | 16.7 | 2.2 | 1.2 | 0 | 24.9 |
| | 6 | 5.4 | 6.6 | 60.8 | 21.9 | 3.6 | 1.8 | 0 | 35.6 |
| | 8 | 6.3 | 7.0 | 55.1 | 24.5 | 4.8 | 2.4 | 0 | 40.2 |
| | 24 | 10.5 | 10.8 | 32.5 | 29.4 | 12.1 | 4.3 | 0.43 | 55.3 |
| | 32 | 11.1 | 12.8 | 27.9 | 28.4 | 15.2 | 4.7 | 0 | 56.9 |

*: the corresponding peaks could not be evaluated due to interferences with the BISTRIS buffer; the area % of the total degradation products were calculated without the compound Unknown 1, as it is most probably not a metabolite of paclitaxel; the compound Unknown 3 is most probably an artefact (e.g. impurity from sample preparation).

TABLE 9

Degradation of liposomal paclitaxel and formation of degradation products at pH 5.0, 5.5 and 6.0 at 2-8° C. (data presented in area %)

| Refrigerator (2-8° C.) | Time [h] | Baccatin | 10-Deacethyl-taxol | Paclitaxel | 7-Epi-Taxol | unknown 1 | unknown 2 | unknown 3 | Total Degradation Products |
|---|---|---|---|---|---|---|---|---|---|
| pH 5.0 | 0 | 0.34 | 0.59 | 96.7 | 2.3 | 0* | 0 | 0 | 3.3 |
| | 1 | 0.35 | 0.43 | 96.7 | 2.5 | 0* | 0 | 0 | 3.3 |
| | 3 | 0* | 0.41 | 96.8 | 2.8 | 0* | 0 | 0 | 3.2 |
| | 6 | 0.38 | 0.50 | 96.7 | 2.4 | 0* | 0 | 0 | 3.3 |
| | 8 | 0* | 0.56 | 97.0 | 2.4 | 0* | 0 | 0 | 3.0 |
| | 24 | 0* | 0.53 | 95.8 | 2.4 | 1.3 | 0 | 0 | 2.9 |
| | 32 | 0* | 0.53 | 95.0 | 2.3 | 2.1 | 0 | 0 | 2.9 |
| pH 5.5 | 0 | 0.31 | 0.59 | 96.8 | 2.3 | 0* | 0 | 0 | 3.2 |
| | 1 | 0.33 | 0.43 | 96.6 | 2.6 | 0* | 0 | 0 | 3.4 |
| | 3 | 0.38 | 0.51 | 96.8 | 2.3 | 0* | 0 | 0 | 3.2 |
| | 6 | 0.38 | 0.55 | 96.7 | 2.3 | 0* | 0 | 0 | 3.3 |
| | 8 | 0* | 0.54 | 97.0 | 2.5 | 0* | 0 | 0 | 3.0 |
| | 24 | 0* | 0.58 | 95.7 | 2.3 | 1.5 | 0 | 0 | 2.9 |
| | 32 | 0* | 0.57 | 95.1 | 2.2 | 2.2 | 0 | 0 | 2.8 |
| pH 6.0 | 0 | 0.34 | 0.62 | 96.7 | 2.3 | 0* | 0 | 0 | 3.3 |
| | 1 | 0.32 | 0.45 | 96.6 | 2.6 | 0* | 0 | 0 | 3.4 |
| | 3 | 0.40 | 0.61 | 96.7 | 2.3 | 0* | 0 | 0 | 3.3 |
| | 6 | 0.40 | 0.54 | 96.7 | 2.4 | 0* | 0 | 0 | 3.3 |
| | 8 | 0* | 0.56 | 96.9 | 2.5 | 0* | 0 | 0 | 3.1 |
| | 24 | 0* | 0.59 | 95.8 | 2.4 | 1.2 | 0 | 0 | 3.0 |
| | 32 | 0* | 0.58 | 95.1 | 2.5 | 1.8 | 0 | 0 | 3.1 |

*the corresponding peaks could not be evaluated due to interferences with the BISTRIS buffer; the area % of the total degradation products were calculated without the compound Unknown 1, as it is most probably not a metabolite of paclitaxel

TABLE 10

Degradation of liposomal paclitaxel and formation of degradation products at pH 6.5 and 7.0 at 2-8° C. (data presented in area %)

| Refrigerator (2-8° C.) | Time [h] | Baccatin | 10-Deacethyl-taxol | Paclitaxel | 7-Epi-Taxol | unknown 1 | unknown 2 | unknown 3 | Total Degradation Products |
|---|---|---|---|---|---|---|---|---|---|
| pH 6.5 | 0 | 0.40 | 0.63 | 96.5 | 2.4 | 0* | 0 | 0 | 3.5 |
|  | 1 | 0.30 | 0.51 | 96.3 | 2.9 | 0* | 0 | 0 | 3.7 |
|  | 3 | 0.43 | 0.67 | 96.3 | 2.6 | 0* | 0 | 0 | 3.7 |
|  | 6 | 0.45 | 0.60 | 96.4 | 2.6 | 0* | 0 | 0 | 3.6 |
|  | 8 | 0* | 0.74 | 96.3 | 3.0 | 0* | 0 | 0 | 3.7 |
|  | 24 | 0* | 0.87 | 94.8 | 2.9 | 1.4 | 0 | 0 | 3.8 |
|  | 32 | 0* | 0.86 | 94.0 | 3.0 | 2.2 | 0 | 0 | 3.9 |
| pH 7.0 | 0 | 0.52 | 0.82 | 95.6 | 3.1 | 0* | 0 | 0 | 4.4 |
|  | 1 | 0.29 | 0.81 | 95.5 | 3.4 | 0* | 0 | 0 | 4.5 |
|  | 3 | 0.56 | 0.89 | 95.2 | 3.4 | 0* | 0 | 0 | 4.8 |
|  | 6 | 0.63 | 1.0 | 94.9 | 3.5 | 0* | 0 | 0 | 5.2 |
|  | 8 | 0* | 1.5 | 92.3 | 5.2 | 1.0 | 0 | 0 | 6.7 |
|  | 24 | 0* | 1.9 | 90.3 | 5.7 | 2.1 | 0 | 0 | 7.6 |
|  | 32 | 2.3 | 1.9 | 87.8 | 5.7 | 2.2 | 0 | 0 | 10.0 |

*the corresponding peaks could not be evaluated due to interferences with the BISTRIS buffer; the area % of the total degradation products were calculated without the compound Unknown 1, as it is most probably not a metabolite of paclitaxel

TABLE 11

Degradation of liposomal paclitaxel and formation of degradation products at pH 7.5 and 8.0 at 2-8° C. (data presented in area %)

| Refrigerator (2-8° C.) | Time [h] | Baccatin | 10-Deacethyl-taxol | Paclitaxel | 7-Epi-Taxol | unknown 1 | unknown 2 | unknown 3 | Total Degradation Products |
|---|---|---|---|---|---|---|---|---|---|
| pH 7.5 | 0 | 0.63 | 0.93 | 93.9 | 3.8 | 0.75 | 0 | 0 | 5.3 |
|  | 1 | 0.62 | 1.1 | 93.0 | 4.3 | 1.0 | 0 | 0 | 5.9 |
|  | 3 | 0.94 | 1.3 | 91.9 | 4.6 | 1.2 | 0 | 0 | 6.9 |
|  | 6 | 1.1 | 1.5 | 91.2 | 4.7 | 1.5 | 0 | 0 | 7.3 |
|  | 8 | 1.4 | 2.1 | 88.0 | 6.8 | 1.7 | 0 | 0 | 10.3 |
|  | 24 | 1.8 | 2.8 | 85.8 | 7.7 | 1.9 | 0 | 0 | 12.4 |
|  | 32 | 2.0 | 3.0 | 85.1 | 7.8 | 2.1 | 0 | 0 | 12.8 |
| pH 8.0 | 0 | 1.3 | 1.9 | 89.0 | 7.1 | 0.80 | 0 | 0 | 10.2 |
|  | 1 | 1.3 | 2.3 | 87.2 | 8.3 | 0.98 | 0 | 0 | 11.8 |
|  | 3 | 2.1 | 2.9 | 84.5 | 9.1 | 1.4 | 0 | 0 | 14.1 |
|  | 6 | 2.5 | 3.5 | 82.3 | 9.7 | 1.7 | 0.35 | 0 | 16.0 |
|  | 8 | 3.8 | 4.8 | 72.6 | 15.2 | 2.4 | 1.1 | 0 | 25.0 |
|  | 24 | 5.1 | 6.7 | 66.3 | 17.2 | 3.3 | 1.4 | 0 | 30.4 |
|  | 32 | 5.5 | 7.6 | 63.9 | 17.1 | 4.3 | 1.6 | 0 | 31.8 |

*: the corresponding peaks could not be evaluated due to interferences with the BISTRIS buffer; the area % of the total degradation products were calculated without the compound Unknown 1, as it is most probably not a metabolite of paclitaxel.

3. Example 3

Increase of In-Use Stability of Paclitaxel Loaded into Cationic Liposomes

In order to investigate the stability of paclitaxel loaded into cationic liposomes under different pH conditions, several additives, preferably additives constituting an acidic pH, are added during preparation. Thereby epimerization at C-7 and the formation of 7-epi-taxol is examined. These compounds may be taken from the group of inorganic and organic acids. Examples for inorganic acids include hydrochloric acid (HCl), phosphoric acid, sulfuric acid, carbonic acid, or other commonly used acids. Examples for organic acids are of the general formula for monobasic acids $R-CO_2H$ with $R=CH_3-(CH_2)_n$; $C_6H_5-(CH_2)_n-$ and n=0-6 for example acetic acid or benzoic acid. In addition, dibasic acids of the general formula $HO_2C-(CH_2)_n-CO_2H$ with n=0-6 such as succinic acid, adipic acid or unsaturated derivatives, such as maleic acid or fumaric acid, or aromatic acids such as phthaleic acid may be employed. Hydroxy carboxylic acids such as citric acid, lactic acid, tartaric acid are also preferred additives.

Preparation:

A liposomal preparation comprising 10 mM DOTAP/DOPC/paclitaxel 50/47/3 is prepared via the ethanol injection method as described earlier. The aqueous solution comprises 10% trehalose (w/v), pH=5.5. The trehalose solution may be adjusted to pH 4.5 through addition of hydrochlorid acid, citric acid, or lactic acid. Following the ethanol injection of a solution of both lipid and active compound, the resulting solution is extruded at 4° C. and lyophilized as described earlier. The lyophilisate is analyzed by PCS for its liposomal size distribution and by HPLC for its paclitaxel and 7-epi-taxol content. The in-use stability of the lyophilisates is established as follows: The lyophilisate (prepared as described earlier) is reconstituted with MilliQ quality water and left for 24 hours at room temperature or 4° C. before examination. Both PCS and HPLC analysis is performed.

Another liposomal preparation has been prepared at room temperature as described earlier with citric acid and lactic acid as additives for the aqueous trehalose solution. Without lyophilizing, these formulations were characterized by their liposomal size and size distribution (PCS) and by drug concentration and 7-epi-taxol content (area %, HPLC).

Result:

When liposomes are prepared at 4° C., lyophilized, and kept in the refrigerator 7-epi-taxol formation is not observed after reconstitution as shown by the data in Table 12. The in-use stability (24 h, rt) of the reconstituted lyophilisates, however, depends on the presence and volatility of the employed additives, as shown in Table 13. Using no additive, 6% 7-epi-taxol is found. This is slightly reduced through the use of volatile hydrochloric acid. After 24 h at room temperature, little or no 7-epi-taxol is found employing solid non-volatile organic acids, such as citric acid or lactic acid (Table 13). Liposomal paclitaxel formulations can be prepared at 25° C. as shown in Table 14 where no degradation of paclitaxel was observed even after storage of 24 h at 25° C. HPLC analysis after 120 h of further storage at 25° C. did not show any 7-epi-taxol (data not shown).

TABLE 12

Paclitaxel-loaded cationic liposomes prepared at 4° C.

| Preparation | pH | $Z_{average}$ [nm] | PI Value | Paclitaxel [%] | 7-epi-taxol [%] |
|---|---|---|---|---|---|
| 10% trehalose | 5.5 | 166 | 0.20 | 100 | 0 |
| 10% trehalose/HCl | 4.5 | 164 | 0.17 | 100 | 0 |
| 10% trehalose/citric acid | 4.5 | 171 | 0.182 | 100 | 0 |
| 10% trehalose/lactic acid | 4.5 | 170 | 0.17 | 100 | 0 |

TABLE 13

In-Use stability (24 h) of paclitaxel-loaded cationic liposomes prepared at 4° C.

| Preparation | pH | $Z_{average}$ [nm] | PI Value | Paclitaxel [%] | 7-epi-taxol [%] |
|---|---|---|---|---|---|
| 10% trehalose | 5.5 | 152 | 0.17 | 93.8 | 6.2 |
| 10% trehalose/HCl | 4.5 | 154 | 0.17 | 95.7 | 4.3 |
| 10% trehalose/citric acid | 4.5 | 159 | 0.16 | 98.7 | 1.3 |
| 10% trehalose/lactic acid | 4.5 | 148 | 0.21 | 100 | 0 |

TABLE 14

In-Use stability (24 h, no lyophilization) of paclitaxel-loaded cationic liposomes prepared at 25° C.

| Preparation | pH | $Z_{average}$ [nm] | PI Value | Paclitaxel [%] | 7-epi-taxol [%] |
|---|---|---|---|---|---|
| 10% trehalose/citric acid | 4.5 | 163.2 | 0.142 | 100 | 0 |
| 10% trehalose/lactic acid | 4.5 | 158.4 | 0.188 | 100 | 0 |

4. Example 4

Preparation of Docetaxel Loaded Cationic Liposomes 4.1 Liposome Preparation Via Lipid Film Method Liposomal formulations comprising docetaxel were prepared using the lipid film method as follows: Lipids of choice and docetaxel are dissolved in chloroform in a round bottom flask. The flask is then rotated under vacuum (100 to 200 mbar, 40° C.) until a thin lipid film is formed. The lipid film is thoroughly dried at 40° C. under full vacuum (3 to 5 mbar) for approximately 30 minutes. The dry lipid film is cooled in an ice bath and is rehydrated with a cold (4° C.) glucose or trehalose solution (pH 5-7) resulting in a suspension of multilamellar lipid vesicles at a total concentration of about 10 to 20 mM. Once a homogeneous dispersion is formed (after 15-20 min rotating) the liposomal dispersion is extruded (filtration under pressure) preferably at a temperature between 4° C. and 8° C. 1-5 times through polycarbonate membranes of appropriate size, typically between 150 and 250 nm, optionally followed by sterile filtration. The low temperature during manufacturing was found to be critical due to increased chemical stability of docetaxel and lipids and due to the finding that a higher active compound to lipid ratio (higher docetaxel content) can be reached. The formed liposomal dispersion is fully characterized by HPLC, PCS and microscopic analysis.

4.2 Liposome Preparation via Ethanol Injection

Liposomal formulations comprising docetaxel were also prepared using the ethanol injection method as follows: docetaxel and lipids were dissolved in ethanol (or another suitable organic solvent) usually at total lipid concentration of about 200-400 mM. An aqueous solution of a cryoprotectant, preferably 10% trehalose, was prepared at pH 5-7 and cooled to a temperature between 4 and 8° C. prior injection of the organic solvent. The ethanolic solution was injected (3-300 ml/min injection speed) into the cold, vigorously stirred trehalose solution reaching a final total lipid concentration of 10 mM. Once a homogeneous dispersion is formed the liposomal dispersion is extruded (filtration under pressure) preferably at a temperature between 4° C. and 8° C. 1-5 times through polycarbonate membranes of appropriate size, typically between 150 and 250 nm, optionally followed by sterile filtration. The low temperature during manufacturing was found to be critical due to increased chemical stability of docetaxel and lipids and due to the finding that a higher active compound to lipid ratio (higher docetaxel content) can be reached. The formed liposomal dispersion is fully characterized by HPLC, PCS and microscopic analysis.

4.3 Variation of Docetaxel Content

Liposomes (10 mM total lipid concentration, 10% trehalose) comprising DOTAP and DOPC are formed with different docetaxel contents. The general composition is defined as 50 mol % DOTAP, (50-X) mol % DOPC and X mol % docetaxel where the docetaxel content is varied from 3 to 13 mol %. Table 15 lists liposomal docetaxel formulations and their typical characteristics, such as average liposomal size, size distribution (PI), active compound and lipid concentration (HPLC), existence of extra-liposomal docetaxel (docetaxel crystals) and their surface charge.

TABLE 15

Liposomal docetaxel formulations

| Docetaxel Content | Liposomal Size (PI) | HPLC, Microscopy | Zeta Potential |
|---|---|---|---|
| 3 mol % | 175 nm (0.20) | according expectation, no crystals | 65 mV |
| 5 mol % | 168 nm (0.20) | according expectation, no crystals | 64 mV |
| 7 mol % | 162 nm (0.24) | according expectation, no crystals | 60 mV |
| 9 mol % | 166 nm (0.18) | according expectation, no crystals | 65 mV |
| 11 mol % | 162 nm (0.20) | according expectation, no crystals | 62 mV |
| 13 mol % | 162 nm (0.14) | according expectation, no crystals | 65 mV |

Employing the lipid film method and the DOTAP/DOPC system, liposomes with up to about 13 mol % docetaxel can be prepared. It is notable, that a higher docetaxel content can be loaded into the liposomal membrane when manufacturing takes place at low temperatures (4° C.-8° C.) compared to higher temperatures (room temperature, 40° C.). The average diameter of docetaxel-containing liposomes is between 160 and 170 nm and the low PI value of ≤0.2 indicates a favorable small size distribution. Determined concentrations (HPLC) are according theoretical values. According HPLC analysis docetaxel, DOTAP and DOPC were chemically stable during the manufacturing process at 4° C. A temperature higher than 10° C. during manufacturing resulted in the formation of docetaxel degradation product as seen in the HPLC chromatograms. All formulations were checked by microscopy (10 fold magnification) for aggregates/crystals. As docetaxel is only little soluble in trehalose or water (~20 µM) the presence of crystals would indicate a significant fraction of docetaxel which is not embedded (solubilized) in the liposomal membrane. Non of the investigated formulations were tested positive for docetaxel crystals. The zeta potential (60-65 mV, Zetasizer 3000, Malvern) did not change with different docetaxel content.

4.4 Lyophilization of Docetaxel-Containing Liposomes

Lyophilization of docetaxel-containing liposomes has been successfully performed applying a procedure as described earlier. As shown in Table 16 liposomal size is not changed whereas the PI value (size distribution) of the respective reconstituted lyophilisate is slightly lowered compared with those of the non-lyophilized formulation.

TABLE 16

Effect of Lyophilization on Liposomal Size and PI Value

| Docetaxel Content | Liposomal Size (PI) | |
| --- | --- | --- |
| | before Lyophilization | after Lyophilization |
| 3 mol % | 175 nm (0.20) | 171 nm (0.10) |
| 5 mol % | 168 nm (0.20) | 162 nm (0.08) |
| 7 mol % | 162 nm (0.24) | 166 nm (0.09) |
| 9 mol % | 166 nm (0.18) | 160 nm (0.08) |
| 11 mol % | 162 nm (0.20) | 156 nm (0.09) |
| 13 mol % | 162 nm (0.14) | 158 nm (0.07) |

Lyophilization has no negative influence on liposomal stability. As checked by HPLC, lipids and docetaxel remain chemically stable.

4.5 Determination of Non-Liposomal Docetaxel

Centrifugation experiments were performed to determine whether there is any free, non-liposomal docetaxel in liposomal docetaxel formulations. This experiment was carried out with Centricon® tubes (centrifugation tubes with a semipermeable membrane which allows small molecules to pass and retains macromolecules). Liposomal formulations (10 mM, 10% trehalose) based on DOTAP and DOPC with 7, 11 and 13 mol % docetaxel were centrifuged at 4500 g and at 4° C. with Centricon® tubes (membrane specification of 30.000 MWCO). After 30 min centrifugation the supernatant was diluted with trehalose the volume of that had been found as permeate. HPLC analysis are summarized in Table 17.

TABLE 17

Determination of non-liposomal Docetaxel (HPLC)

| Docetaxel Content | Supernatant | Permeate | non-liposomal fraction |
| --- | --- | --- | --- |
| 7 mol % | 0.719 mM | 0.026 mM | 4% |
| 11 mol % | 1.040 mM | 0.038 mM | 3% |
| 13 mol % | 1.305 mM | 0.059 mM | 4% |

The results show that docetaxel can be incorporated into the liposome membrane at a concentration of at least 13 mol % without increasing the fraction of nonliposomal docetaxel.

4.6 Physicochemical Stability of Docetaxel Formulations

Figure 3B:
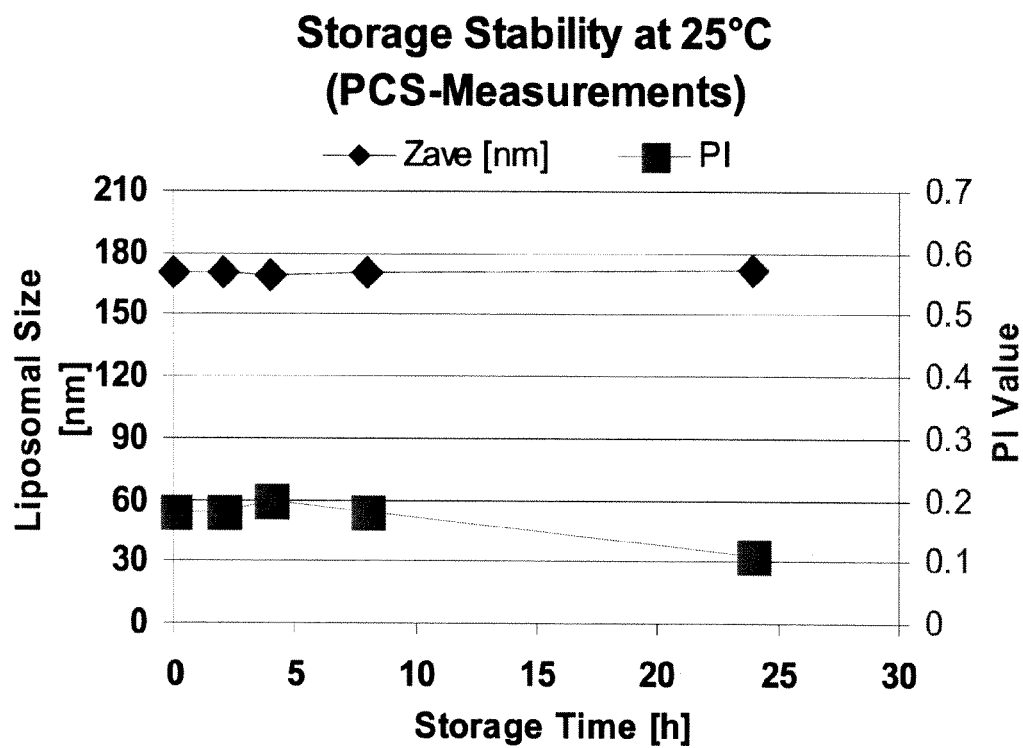
Figure 3C:
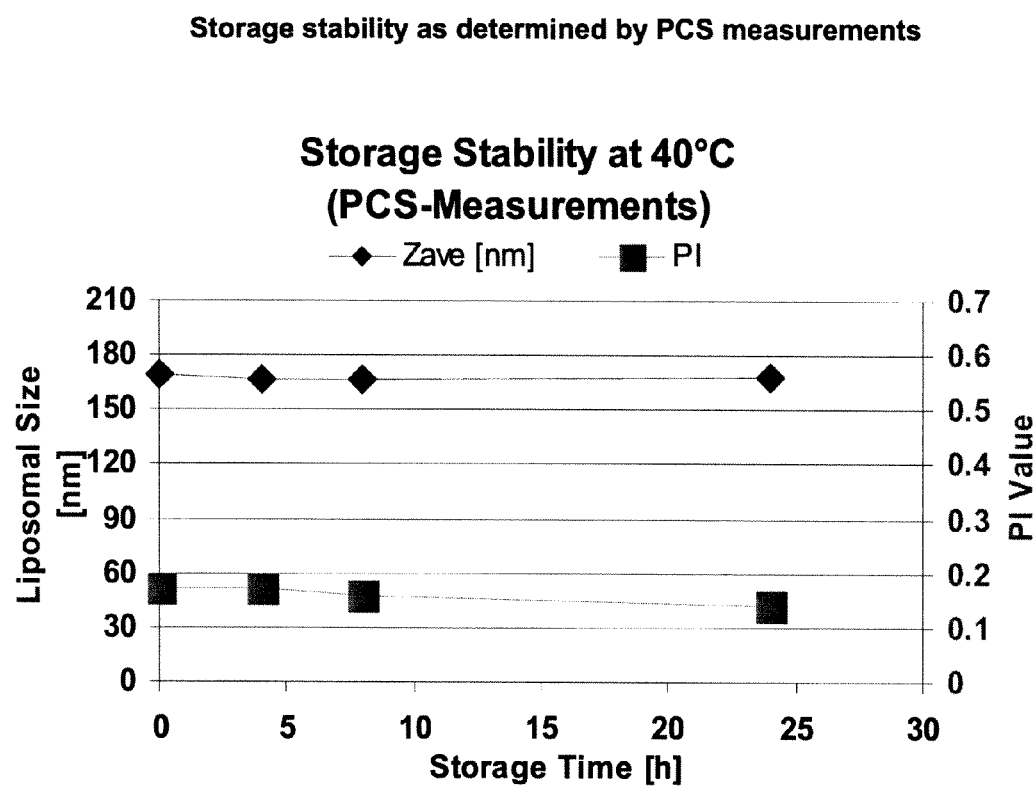

A liposomal formulation containing 5 mol % docetaxel has been used to study the physicochemical stability. A first experiment revealed that the content of docetaxel in the formulation has no influence on the stability. Also no difference has been found for the liquid (non-lyophilized) and the freeze-dried formulation. Storage stability at 4° C., 25° C. and 40° C. has been characterized by PCS (liposomal size and size distribution), light blockage measurements (PAMAS device), microscopy and HPLC. The physical stability is shown in FIG. 3. At all temperatures, the liposomal size and size distribution did not change within 24 h.

In principle, an increased particle number in the formulation as measured by light blockage measurements (PAMAS device) indicates a poor physical stability due to ongoing aggregation of liposomes resulting in larger aggregates (larger than 1 µm). Using an adequate experimental setup no such increase has been found. FIG. 4 shows particles numbers that have been found during storage at 25° C. The particle count after 24 h is in the same range compared with the 8 h value.

HPLC analysis of the formulation at different time point clearly revealed a good chemical stability at 4° C. At 40° C. increase of degradation of up to 20% has been observed after storing of 24 h.

4.7 In vitro Experiments

The efficacy of the liposomal docetaxel formulation is determined in vitro by analyzing the decrease of cell viability in correlation to the active compound concentration. The active compound concentration at which cell viability is inhibited to 50% ($IC_{50}$) is used as index for the inhibitory potential.

C-26 (murine colon carcinoma cell line) and Ea.Hy 926 cells (transformed human endothelial cell line) are seeded at a constant density ($2 \times 10^4/cm^2$) in 24-well plates and cultivated over night at conditions of 5-5.5% $CO_2$, 37° C. and ~90% humidity. At day 1, cell culture medium is replaced by a mixture of fresh medium and a series of 11 consecutive active compound dilutions is added to each well (duplicates) to cover a range between 0.1 and 1000 nM final active compound concentration. After 72 h, the cell viability in each well is determined by measuring the activity of mitochondrial dehydrogenases (MIT assay). In viable cells the MTT substrate is converted to a blue, cell impermeable dye (Formazan). After 1 h the medium is removed, cells are lysed with isopropanol/0.04% HCl and the amount of the blue Formazan given as optical density at a wavelength of 550 nm ($OD_{550\,nm}$) is quantitated in an ELISA reader. The experiment is evaluated using the Sigma Plot analysis software by plotting the mean $OD_{550\,nm}$ value against the respective active compound concentration. A best fit curve is calculated based on a double-sigmoid assumption algorithm and the $IC_{50}$ value is determined according to this best fit curve with results as shown in Table 18.

TABLE 18

$IC_{50}$ Values of Taxotere and docetaxel loaded liposomes

| Formulation | $IC_{50}$ (C-26) | $IC_{50}$ (EA.hy 926) |
| --- | --- | --- |
| Taxotere ® | 5 nM | 4 nM |
| Liposomal Docetaxel Formulation | 4 nM | 7 nM |

$IC_{50}$ values clearly reveal equal efficacy of docetaxel formulated with Polysorbate 80 (Taxotere ®, Aventis) and liposomal docetaxel formulation (composition: DOTAP/DOPC/docetaxel 50:39:11) in both cell lines, C-26 and EA.hy 926.

4.8 In vivo Experiments (A-375 Melanoma of Nude Mice)

Materials and Methods:

NMRI-nude mice were purchased from Elevage Janvier and housed in isolated ventilated cages under save environmental conditions (SPF facility, 22° C., 30-70% humidity, 12 h light/dark cycle) with food and water ad libitum. Experimental design was reviewed and approved by local government.

Tumor cells (A-375 human melanoma cell line, ATCC Nr.: CRL-1619) were grown as described in the data sheet supplied by ATCC. Tumor cells ($5 \times 10^6$ in PBS) were inoculated s.c. in the right dorsal flank of mice in a volume of 50 μl on day 0.

Mice were assigned to the experimental groups (8 animals per cage), housed and handled (including monitoring of the body weight gain) at least five days before tumor inoculation (=day −6 to 0). Treatment begins after the tumors reached a volume of approximately 100 mm³. Drugs and liposomal preparations were given by five iv injection, every other day at equivalent doses. The liposomal preparations were prepared as described previously. The solutions were administered slowly in a volume of ~5 μl/g body weight. Animals were clinically monitored during the whole experiment and for at least one week after treatment was finished. Monitoring of tumor size was performed three times a week after staging and before application during treatment period (at least one week). The tumor dimensions were measured by calliper and the tumor size was calculated according to the following formula: $V = \pi L W^2 / 6$ (L=greatest length, W=width of perpendicular axis). The body weight of individual animals was monitored at least twice during handling period (e.g. day −6 and 0), after tumor inoculation and after start of treatment for all groups. EDTA blood was collected from the retrobulbar plexus at four different points: during handling (day −3), tumor staging (day 14) and in the middle of treatment (~day 19) from 4 animals of all treatment groups for haematology. The number of red and white blood cells and platelets were determined using an automated cell counter (Abbott Cell Dyn 3500). The results are shown in FIG. 5.

Whereas tumors in the control group showed a rapid and progressive tumor growth, LipoDoc™ (DOTAP:DOPC:docetaxel 50:39:11) showed a strong reduction in the tumor growth rate, Taxotere® reduced the tumor growth only to a limited extent.

TABLE 19

Experimental groups and dose

| Group | Formulation | Dose [mg/kg] | N° of mice |
|---|---|---|---|
| 0 | 10% trehalose | — | 8 |
| 1 | LipoDoc ™ | 5 | 8 |
| 2 | Taxotere ® | 5 | 8 |

5. Example 5

Liposomal Paclitaxel (5 mol %)

5.1 Liposome Preparation via Ethanol Injection

A liposomal formulation comprising 5 mol % paclitaxel was prepared using the ethanol injection method as follows: paclitaxel and lipids of a molar ratio of 50:45:5 DOTAP/DOPC/paclitaxel were dissolved in ethanol (or another suitable organic solvent) usually at total lipid concentration of about 200-400 mM. An aqueous solution of a cryoprotectant, preferably 10% trehalose, pH 5-7, was prepared and cooled to a temperature between 4 and 8° C., preferably 4° C., prior injection of the organic solvent. The ethanolic solution was injected (3-300 ml/min injection speed) into the cold, vigorously stirred trehalose solution. Once a homogeneous dispersion is formed the liposomal dispersion is extruded (filtration under pressure) preferably at a temperatures between 4° C. and 8° C., preferably 4° C., 1-5 times through polycarbonate membranes of appropriate size, typically between 150 and 250 nm, optionally followed by sterile filtration. In addition to the manufacturing temperature of about 4° C. temperatures of 25° C. and 40° C. were evaluated for their effect on the product quality. The formed liposomal dispersions were fully characterized by HPLC, PCS and microscopic analysis.

5.2 Effect of Temperature on the Preparation Process

In process control during the preparation procedure was done after ethanol injection, after extrusion and after lyophilization.

After Ethanol Injection:

At all three temperatures ethanol injection resulted in liposomes with a liposomal size of about 220 nm and a broad size distribution (PI) of about 0.4-0.6 (according PSC measurements). HPLC analysis revealed paclitaxel degradation when formulated at 40° C. while at 4 and 25° C. chemical stability of each constituent has been proofed. Microscopy showed little amount of paclitaxel crystals at 40° C. but not at 4 and 25° C.

After Extrusion:

At 40° C. difficulties occurred during extrusion due to clogged membranes. Replacing the clogged membrane did not solve the problem. Microscopy of the liposomal solution that did not pass the membrane revealed an increased amount of non-liposomal paclitaxel crystals that obviously blocked the membrane. Extrusion at 40° C. was not feasible. This was not the case when extrusion was performed at lower temperatures. In that case HPLC analysis gave concentration according expectations without any loss of material by the extrusion procedure (5 times, 0.2 μm membrane). PCS data after extrusion at 4 and 25° C. were comparable: Liposomal size of about 170 nm and a small size distribution (PI) of about 0.1-0.2.

After Lyophilization:

Lyophilization of the formulation prepared at 4° C. and 25° C. has been successfully performed using a procedure described in example and characterized by HPLC, PCS and microscopic analysis.

5.3 In vivo Experiments 5.3.1 Therapeutic Efficacy of LipoPac™ in A-375 Melanoma of Nude Mice Materials and Methods:

NMRI-nude mice were purchased from Elevage Janvier and housed in isolated ventilated cages under save environmental conditions (SPF facility, 22° C., 30-70% humidity, 12 h light/dark cycle) with food and water ad libitum. Experimental design was reviewed and approved by local government.

Tumor cells (A-375 human melanoma cell line, ATCC Nr.: CRL-1619) were grown as described in the data sheet supplied by ATCC. Tumor cells ($5 \times 10^6$ in PBS) were inoculated s.c. in the right dorsal flank of mice in a volume of 50 μl on day 0.

Mice were assigned to the experimental groups (8 animals per cage), housed and handled (including monitoring of the body weight gain) at least five days before tumor inoculation (=day −6 to 0). Treatment begins after the tumors reached a volume of approximately 100 mm³. Drugs and liposomal preparations were given by iv injection, three times a week (Mo, Wed, Fri) for the following three weeks at equivalent doses. The liposomal preparations were prepared as described above. The solutions were administered slowly in a volume of ~10 μl/g body weight.

Animals were clinically monitored during the whole experiment and for at least one week after treatment was finished. Monitoring of tumor size was performed three times a week after staging, before application during treatment period and during recovery period (at least one week). The tumor dimensions were measured by calliper and the tumor size was calculated according to the following formula: $V=\pi LW^2/6$ (L=greatest length, W=width of perpendicular axis). The body weight of individual animals was monitored at least twice during handling period (e.g. day −6 and 0), after tumor inoculation, after start of treatment and during recovery period (at least one week) for all groups. EDTA blood was collected from the retrobulbar plexus at four different points: during handling (day −3), tumor staging (day 7), in the middle of treatment (~day 21), and at the end of the recovery period (day 28) from 4 animals of all treatment groups for haematology. The number of red and white blood cells and platelets were determined using an automated cell counter (Abbott Cell Dyn 3500).

Whereas tumors in the control group showed a rapid and progressive tumor growth, LipoPac™ (DOTAP:DOPC:paclitaxel 50:45:5) showed a strong reduction in the tumor growth rate, Taxol® reduced the tumor growth only to a limited extent (Table 20, FIG. 6).

TABLE 20

Experimental groups and dose

| Group | Formulation | Dose [mg/kg] | N° of mice |
|---|---|---|---|
| 0 | 10% trehalose | — | 8 |
| 1 | LipoPac ™ | 5 | 8 |
| 2 | Taxol ® | 5 | 8 |

5.3.2 Therapeutic Efficacy of Lipopac in B-16 Melanoma of C57/BL6 mice
Materials and Methods:

C57/Black6 mice were purchased from Charles River and housed in isolated ventilated cages under save environmental conditions (SPF facility, 22° C., 30-70% humidity, 12 h light/dark cycle) with food and water ad libitum. Experimental design was reviewed and approved by local government.

Tumor cells (B-16 human melanoma cell line: CRL-6322) were grown as described in the data sheet supplied by ATCC. Tumor cells ($5\times10^6$ in PBS) were inoculated s.c. in the right dorsal flank of mice in a volume of 50 µl on day 0.

Treatment start on day 6 after tumor cell injection. Three injections per week until end of experiment. End of study was planned to be determined by tumor size of the animals and ethical considerations.

Mice were assigned to the experimental groups (8 animals per cage), housed and handled (including monitoring of the body weight gain) at least five days before tumor inoculation (=day −6 to 0). The liposomal preparations were prepared as described above. The solutions were administered slowly in a volume of ~10 µl/g body weight.

Animals were clinically monitored during the whole experiment. Monitoring of tumor size was performed three times a week after staging and before application during treatment period. The tumor dimensions were measured by calliper and the tumor size was calculated according to the following formula: $V=\pi LW^2/6$ (L=greatest length, W=width of perpendicular axis). The body weight of individual animals was monitored at least twice during handling period (e.g. day −6 and 0), after tumor inoculation and after start of treatment for all groups. EDTA blood was collected from the retrobulbar plexus at four different points: during handling (day −3), tumor staging (day 6) and in the middle of treatment (~day 14) from 4 animals of all treatment groups for haematology. The number of red and white blood cells and platelets were determined using an automated cell counter (Abbott Cell Dyn 3500).

Whereas tumors in the control group showed a rapid and progressive tumor growth, LipoPac™ (DOTAP:DOPC:paclitaxel 50:45:5) showed a strong reduction in the tumor growth rate, Taxol® reduced the tumor growth only to a limited extent (Table 21, FIG. 7).

TABLE 21

Experimental groups and dose

| Group | Formulation | Dose [mg/kg] | N° of mice |
|---|---|---|---|
| 0 | 10% trehalose | / | 8 |
| 1 | LipoPac ™ | 5 | 8 |
| 2 | Taxol ® | 5 | 8 |

6. Example 6

Preparation of Liposomes Comprising Cationic Lipids and Lipophilic Camptothecin or Camptothecin-Derivatives The preparation of liposomes comprising cationic lipids and lipophilic camptothecin (CPT) or CPT-derivatives in the pH range between 3-7 is described. The CPT is loaded into the liposome. Liposomes can be prepared by different methods. All techniques have in common, that a mixture of lipids plus active compound is provided in a suitable organic solvent and then dispersed in an aqueous medium. Subsequently, further processing, like extrusion, sterile filtration or lyophilization may be applied. The active compound/lipid ratio is adjusted by mixing suitable amounts of lipid and active compound in an organic solvent. Typical molar active compound/lipid ratios range from 1:1000 to 1.10.

Subsequently, two methods are described to more detail for preparations with Camptothecin. The disclosed methods may be applied to any CPT-derivative, which is lipophilic at the desired pH.
6.1 Liposome Formation
6.1.1 Film Method From the organic solution comprising lipid plus active compound, the solvent is evaporated, and a thin film of lipid plus active compound is formed at the inner wall of a flask. The thin molecular film is resuspended in an aqueous phase, which can contain further components such as buffers, ions, cryoprotectants and the like. With this procedure, liposome suspensions are formed in a self-assembly process. A standard preparation is obtained by forming a film of 99.5 µM DOTAP and 0.5 µM Camptothecin from a solution in $CHCl_3$/MeOH (10:1). The film is then reconstituted with 10 ml of the aqueous phase, in order to achieve a suspension where the total liposomal concentration (lipid+active compound) is 10 mM. The aqueous solution comprises a cryoprotectant, e.g. glucose or trehalose and (optionally) a buffer, to achieve a desired pH after reconstitution. For camptothecin in the lactone form, a pH of 5-6 is used. For other formulations and CPT derivates, the pH can vary in the range between 3 and 7.

A liposomal preparation with an active compound/lipid ratio of 1:200, and with a total (lipid+active compound) concentration of 10 mM is obtained. Other typical total molarities are 15 mM, 20 mM or 25 mM. If necessary, molarities up to 50 mM or higher can be formulated. The molar percentage of the active compound can be in the rage from 0.1 to 10, depending on the experimental necessities (assignment of the liposomes, type of CPT-derivate). The lipid phase can comprise only one cationic lipid, such as DMTAP, DOTAP, DPTAP, DSTAP, DOTMA, or DDAB, or it can comprise up to 60% of charged and/or non-charged colipids. Standard preparations which have been used most frequently comprise DOTAP/DOPC=1:1 or DOTAP/Chol 1:1. Accordingly, other cationic lipids, such as DMTAP, DSTAP, DDAB, DOTMA and the like can be used.

6.1.2 Organic Solution Injection

Liposomal dispersions can be prepared by injection of a solution comprising lipid plus active compound in an organic solvent, into an aqueous solution, pH 3-7, preferably 5-6 for camptothecin lactone. A typical solvent is ethanol ('ethanol injection'). The solution has a (lipid) concentration between 200-400 mM. A suitable volume of the solution is injected under vigorous stirring. All compositions and concentrations as described in the previous section can be prepared by this approach. As an alternative to ethanol, other suitable solvents or mixtures thereof can be taken. Typically, these are alcohols, ethers, chloroform, hydrocarbons, etc. As well solvents in the supercritical state can be applied, such as hydrocarbons, carbon dioxide, perfluorinated compounds, etc. Subsequently to the described preparation procedure, extrusion dialysis, a concentration step or freeze drying can be performed.

6.1.3 Extrusion

The liposomal preparations as prepared by the above-described methods do not have necessarily the desired size distribution. Therefore, an extrusion through a membrane of defined pore size can be performed subsequently. Usually at least one extrusion through a membrane with a pore size of 200 nm (Osmonics Inc., Poretics, polycarbonate 0.2 µm) is performed. Other typical extrusion membranes have a pore size of 100 nm or 400 nm. Size distributions are controlled by quasi-elastic light scattering (Malvern, Herrenberg, Germany).

Further processing, like sterile filtration or lyophilization can be performed.

The liposomal preparation can be lyophilized and reconstituted with water to the original state without changing the sized distribution and the active compound/lipid ratio.

6.2 Characterization

The size distribution of the liposomal preparations is determined by quasi-elastic light scattering (Malvern, Herrenberg, Germany) and the composition is controlled by HPLC. As a further control for successful loading, UV-VIS spectroscopy is applied, enabling the determination of camptothecin in the liposomal preparation in-situ. Different spectra for the active compound in the stock solution, in the liposome, and after dissolving the liposome preparation in organic solvent are found. As an example, data from a liposomal preparation comprising camptothecin with a active compound/lipid ratio of 1:1000 are given. With this active compound/lipid ratio, the spectroscopic measurements could be performed without further dilution of the samples. The preparation comprising 10 mM DOTAP/DOPC 1:1 was produced by the film method in an aqueous solution of trehalose at pH 5.5. The preparation was extruded 5 times through a membrane with a pore size of 200 nm (Osmonics Inc). By quasi-elastic light scattering a $Z_{ave}$ of 156 nm with a PI of 0.15 was determined. In the figure, the spectra of camptothecin in stock solution ($CHCl_3$/MeOH), in the liposomal preparation, and after dissolving the liposomes in THF/MeOH/HCl (1:5) are shown. For the measurement of the liposomal preparation, an empty preparation (pure DOTAP/DOPC) with the same lipid composition was used for the blank measurement. In the same way, for the measurement in THF/MeOH/HCl, the empty liposomes were dissolved for the blank measurement. For better comparison, the spectra are vertically shifted and the data from the measurement after dilution of the liposomes in THF/MeOH/HCl are multiplied by 5. As can be seen in FIG. 8, different spectra are obtained for the three cases. A characteristic peak shape for the liposomal camptothecin can be seen (FIG. 8, spectrum b). After dissolving the liposomes in THF/MeOH/HCl, a further spectral shift is obtained.

6.2.1 Example: Improvement of Chemical Stability of Epothilones in Cationic Liposomes Encapsulation of epothilone B is disclosed as specific example. However, other epothilones known in the art such as epothilone A, E or F or derivatives of epothilone A, B, E or F can be encapsulated in the same manner [14, 11, 13, 15].

Cationic liposomes containing epothilone B were prepared according to the film method. Briefly, for 10 ml of a 10 mM liposome suspension, 95 µmol of DOTAP and 5 µmol of epothilone B were dissolved in 15 ml chloroform in a round bottom flask. The chloroform was evaporated using a rotary evaporator and the resulting thin lipid film was dried for 60 min at 7-10 mbar. Subsequently, the lipid film was dissolved in 10 ml aqueous solution (see Table 22) The suspension was 5 times extruded (Northern Lipids Extruder) through 200 nm polycarbonate membranes (Osmonics Inc.). Liposome composition and size were checked by HPLC and PCS.

TABLE 22

Summary of Epothilone B Liposomes

| Formulation | Components of aqueous solution | Epothilone B concentration | Half life of Epothilone B |
|---|---|---|---|
| DOTAP/epothilone B = 95/5 mol % | 10% trehalose, pH 5.5 | 0.5 mM = 200 mg/l | 600 days |
| DOTAP/epothilone B = 95/5 mol % | 10% trehalose and 10 mM Tris/HCl buffer, pH 7.0 | 0.5 mM = 200 mg/l | 285 days |

Stability Assay.

In the formulations, the chemical stability of epothilone B was investigated. The formulations were aliquoted and half of the aliquots was stored at −80° C. (reference formulations). The other half (test formulations) was stored at 4-8° C. At selected time points, epothilone B concentration was determined by HPLC in a respective test formulation and in a reference formulation. The epothilone B concentration found in the test formulation was expressed as % of the epothilone B concentration in the reference formulation (assumed to be 100° A:). The last column of Table 22 displays the half life of epothilone B, defined as the time point at which the epothilone B concentration in the test formulation amounted to 50% of the epothilone B concentration in the respective reference formulation.

The data shows that when comparing the epothilone stability in liposomal formulations, at lower pH (5.5) the stability was better than that at higher pH (7.0). This is in strong contrast to the literature where an increasing instability of epothilones at low pH is described.

REFERENCES

1. Sharma, A. and R. M. Straubinger, *Novel Taxol Formulations—Preparation and Characterization of Taxol-Containing Liposomes*. Pharmaceutical Research, 1994. 11(6): p. 889-896.

2. Thurston, G., et al., *Cationic liposomes target angiogenic endothelial cells in tumors and chronic inflammation in mice.* J Clin Invest, 1998. 101(7): p. 1401-13.
3. Campbell, R B., S. V. Balasubramanian, and R. M. Straubinger, *Influence of cationic lipids on the stability and membrane properties of paclitaxel-containing liposomes.* J Pharm Sci, 2001. 90(8): p. 1091-105.
4. Dordunoo, S, and H. M. Burt, *Solubility and Stability of taxol: effects of buffers and cyclodextrins.* International Journal of Pharmaceutics, 1996. 133: p. 191-201.
5. Vernooij, E., et al., *Chemical hydrolysis of DOTAP and DOPE in a liposomal environment.* Journal of Controlled Release, 2002. 79(1-3): p. 299-303.
6. Sharma, A., E. Mayhew, and R. M. Straubinger, *Antitumor effect of taxol-containing liposomes in a taxol-resistant murine tumor model.* Cancer Res, 1993. 53(24): p. 5877-81.
7. Grit, M., Crommelin, D. J. A., *Chemical stability of liposomes: implicatins for their physical stability.* Chemistry and Physics of Lipids, 1993. 64: p. 3-18
8. N. J. Zuidam, D. J. A Crommelin, *Chemical Hydrolysis of Phospholipids.* Journal of Pharmaceutical Sciences, 1995. 84: p. 1113-1119.
9. M. Sefkow, M. Kiffe, G. Höfle, *Derivatization of the C12-C13 functional groups of epothilones A, B and C.* Bioorg. & Medicinal Chem. Lett., 1998, 8: 3031-3036.
10. A. Regueiro-Ren et al., *SAR and pH Stability of Cyano-Substituted Epothilones.* Org. Lett. 2002, 4: 3816-3818.
11. K. C. Nicolaou, A. Ritzen, K. Namoto *Recent developments in the chemistry, biology and medicine of the epothilones.* Chem. Comm. 2001, 1523-1535.
12. F. Y. F. Lee et al., *BMS-247550: A novel epothilone analog with a mode of action similar to paclitaxel but possessing superior antitumor activity.* Clin. Cancer Res. 2001, 7: 1429-1437.
13. T.-C-Chou et al., *The synthesis, discovery and development of a highly promising class of microtubule stabilization agents.* PNAS 2001, 98: 8113-8118.
14. K.-H. Altmann, M. Wartmann, T. O'Reilly. *Epothilones and related structures.* Biochim. Et Biophys. Acta 2000, 1470: M79-M91.
15. S. J. Stachel et al., On the total synthesis and preliminary biological evaluations of 15(R) and 15(S) Aza-dEpoB. Org. Lett. 2000, 2: 1637-1639.

The invention claimed is:

1. A method for producing a cationic liposomal preparation comprising:
   (a) mixing an organic solvent with a lipophilic active compound and a cationic lipid to form an organic solution;
   (b) mixing the organic solution of step (a) with an aqueous solution comprising a stabilizing agent to form a dispersion of cationic liposomes, wherein the dispersion comprises cationic liposomes in an aqueous medium;
   (c) optionally homogenising the dispersion of step (b) at least once;
   (d) optionally sterile filtrating the dispersion obtained in step (c); and
   (e) optionally dehydrating the dispersion of cationic liposomes of step (d) to form a cationic liposomal preparation;
   wherein the cationic liposomes in the dispersion of step (b) comprise at least one cationic lipid in an amount of at least about 30 mol % and a lipophilic active compound in an amount of at least about 0.1 mol %; and wherein the stabilizing agent in the dispersion of step (b) is present in an amount of about 0.1% (m/v) to about 20% (m/v); and, wherein the pH value of the aqueous medium in any one of steps (b), (c), or (d) is between about 3.0 and 7.0.

2. The method of claim 1, wherein the pH value of the aqueous medium in any one of steps (b), (c), or (d) is between about 3.0 and about 6.5 between about 4.0 and about 6.5, between about 4.0 and about 6.0, or between about 4.5 and about 5.5.

3. The method of claim 1, wherein the pH value of the aqueous medium in step (b) is between about 3.0 and about 6.5, between about 4.0 and about 6.5, between about 4.0 and about 6.0, or between about 4.5 and about 5.5.

4. The method of claim 1, wherein the cationic liposomes comprise a further amphiphile in an amount of up to about 69.9 mol %.

5. The method of claim 1, wherein the method further comprises reconstituting the cationic liposomal preparation of step (c) in an aqueous solution.

6. The method of claim 1, wherein the method further comprises ultra filtrating the dispersion before step (c) and/or (d).

7. The method of claim 1, wherein the liposomal preparation comprising the active compound is physically and chemically stable in any one of the steps (b), (c), or (d) for at least about 12 hours at about 2° C. to about 8° C. or at least about 4 hours at ambient temperature.

8. The method of claim 1, wherein at least one of the steps (b), (c), or (d) is performed at a temperature between about −1° C. and about 15'C. between about 1° C. and about 10° C., or between about 2° C. and about 8° C.

9. The method of claim 4, wherein the further amphiphile is non-cationic.

10. The method of claim 1, wherein the lipophilic active compound is selected from the group consisting of a taxane, a camptothecin, an epothilone, a statin, a depsipeptide, thalidomide, other agents interacting with microtubuli such as discodermolide, laulimalide, isolaulimalide, eleutherobin, Sarcodictyin A, and Sarcodictyin B.

11. The method of claim 1, wherein the taxane is paclitaxel, docetaxel, or any lipophilic derivative thereof.

12. The method of claim 10, wherein the liposomal preparation comprising the taxane is physically and chemically stable in any one of the steps (b), (c), or (d) for at least about 12 hours at about 2° C. to about 8° C. and at least about 4 hours at ambient temperature.

13. The method of claim 1, wherein the liposomal preparation comprises liposomes with an average particle size of about 50 nm to about 400 nm or about 100 nm to about 300 nm.

14. The method of claim 9, wherein the non-cationic amphiphile is a sterol, a phospholipid, a lysolipid, a lysophospholipid, a sphingolipid, as pegylated lipid, or a combination thereof.

15. The method of claim 14, wherein the sterol is cholesterol.

16. The method of claim 14, wherein the phospholipid is diacylphosphatidylcholine.

17. The method of claim 1, wherein step (c) is performed by freeze drying.

18. The method of claim 1, wherein step (c) comprises removing water under vacuum.

19. The method of claim 1, wherein the cationic liposomal preparation comprises a non-volatile organic acid and/or the aqueous solution.

20. The method of claim 19, wherein the non-volatile organic acid is citric acid.

21. The method of claim 5, wherein reconstitution of the cationic liposomal preparation is performed at a temperature between about −1° C. and about 15° C., between about 1° C. and about 10° C., or between about 2° C. and about 8° C.

22. The method of claim 5, wherein the pH value of the aqueous solution is between about 3.0 and about 6.5, between about 4.0 and about 6.5, between about 4.0 and about 6.0, or between about 4.5 and about 5.5.

\* \* \* \* \*